(12) United States Patent
Wojczak

(10) Patent No.: US 11,896,104 B2
(45) Date of Patent: Feb. 13, 2024

(54) SANITIZING HAIR DRYER

(71) Applicant: CONAIR CORPORATION, Stamford, CT (US)

(72) Inventor: Sophia Wojczak, Harrison, NY (US)

(73) Assignee: Conair LLC, Stamford, CT (US)

(*) Notice: Subject to any disclaimer, the term of this patent is extended or adjusted under 35 U.S.C. 154(b) by 693 days.

(21) Appl. No.: 16/993,593

(22) Filed: Aug. 14, 2020

(65) Prior Publication Data

US 2022/0047055 A1 Feb. 17, 2022

(51) Int. Cl.
*A45D 20/12* (2006.01)
*A61L 2/10* (2006.01)
*A61L 9/20* (2006.01)

(52) U.S. Cl.
CPC ............... *A45D 20/12* (2013.01); *A61L 2/10* (2013.01); *A61L 9/20* (2013.01); *A45D 2200/205* (2013.01); *A61L 2202/11* (2013.01); *A61L 2202/16* (2013.01); *A61L 2209/12* (2013.01)

(58) Field of Classification Search
CPC ..... A45D 20/12; A45D 2200/205; A61L 2/20; A61L 2/10; A61L 9/20; A61L 2202/11; A61L 2202/16; A61L 2202/12
USPC .......................................................... 34/380
See application file for complete search history.

(56) References Cited

U.S. PATENT DOCUMENTS

| | | |
|---|---|---|
| 2,248,618 A | 7/1941 | Fischer |
| 2,553,711 A | 5/1951 | Jackson |
| 2,560,808 A * | 7/1951 | Maccallum ............ A45D 20/22 34/100 |
| 2,688,971 A | 9/1954 | Daniels et al. |
| 2,742,708 A | 4/1956 | McCormick |
| 4,210,429 A | 7/1980 | Golstein |
| 4,382,174 A | 5/1983 | Barns |
| 4,506,454 A * | 3/1985 | Kerschgens ............ A61N 5/06 34/68 |
| 4,595,838 A | 6/1986 | Kerschgens |
| 4,694,179 A | 9/1987 | Lew et al. |

(Continued)

FOREIGN PATENT DOCUMENTS

| | | |
|---|---|---|
| CN | 2702645 Y | 6/2005 |
| DE | 2732895 A1 | 1/1979 |

(Continued)

OTHER PUBLICATIONS

Ultraviolet wavelength range by Google search dated Mar. 2, 2023.*

(Continued)

*Primary Examiner* — Stephen M Gravini
(74) *Attorney, Agent, or Firm* — Grogan, Tuccillo & Vanderleeden, LLP

(57) ABSTRACT

A hair dryer includes a housing having a handle portion and a nozzle portion, a motor within the housing, a fan drivingly connected to the motor within the housing, a heating element within the housing, and at least one ultraviolet light emitting element within the nozzle portion, the at least one ultraviolet light emitting element being configured to irradiate a flow passage of the nozzle portion with ultraviolet light. At least a portion of the housing adjacent to the at least one ultraviolet light emitting element is transparent or translucent allowing the ultraviolet light to be viewed from exterior to the housing.

20 Claims, 26 Drawing Sheets

(56) References Cited

U.S. PATENT DOCUMENTS

| | | | |
|---|---|---|---|
| 4,731,541 A * | 3/1988 | Shoemaker | A45D 29/00 |
| | | | 250/455.11 |
| 4,786,812 A | 11/1988 | Humphreys | |
| 4,806,768 A | 2/1989 | Keutenedjian | |
| 4,910,382 A | 3/1990 | Kakuya et al. | |
| 5,112,370 A | 5/1992 | Gazzano | |
| 5,165,395 A | 11/1992 | Ricci | |
| 5,505,904 A | 4/1996 | Haidinger et al. | |
| 6,053,180 A | 4/2000 | Kwan | |
| 6,886,373 B2 * | 5/2005 | Carrubba | D06F 73/00 |
| | | | 68/5 R |
| 7,328,708 B2 | 2/2008 | Malak | |
| 7,731,379 B2 * | 6/2010 | Wakalopulos | B05D 3/067 |
| | | | 118/620 |
| 8,387,271 B2 | 3/2013 | Shami et al. | |
| 8,973,284 B2 | 3/2015 | Shami et al. | |
| 9,557,106 B2 | 1/2017 | Stewart | |
| 10,335,618 B2 | 7/2019 | Zhou et al. | |
| 10,548,439 B2 | 2/2020 | Gagnon et al. | |
| 10,731,920 B2 * | 8/2020 | Sanfilippo | F26B 5/12 |
| 11,589,662 B2 * | 2/2023 | Kim | A45D 20/122 |
| 2001/0043887 A1 | 11/2001 | Morneault et al. | |
| 2002/0098127 A1 | 7/2002 | Bollini | |
| 2004/0065271 A1 | 4/2004 | Cheng | |
| 2008/0092915 A1 | 4/2008 | Chan | |
| 2009/0205664 A1 | 8/2009 | Lyon | |
| 2010/0170104 A1 | 7/2010 | Shami et al. | |
| 2015/0069263 A1 | 3/2015 | Moyal | |
| 2022/0023456 A1 * | 1/2022 | Wojczak | A61L 2/10 |
| 2022/0047055 A1 * | 2/2022 | Wojczak | A45D 20/12 |

FOREIGN PATENT DOCUMENTS

| | | | | |
|---|---|---|---|---|
| DE | 3404214 A1 * | 8/1985 | | |
| EP | 3721748 A2 * | 10/2020 | | A45D 20/10 |
| GB | 2103095 A | 2/1983 | | |
| GB | 2211419 A | 7/1989 | | |
| JP | 2006068187 A | 3/2016 | | |
| JP | 2020171532 A * | 10/2020 | | A45D 20/10 |
| KR | 20130115845 | 10/2013 | | |
| KR | 20140040326 A * | 4/2014 | | |

OTHER PUBLICATIONS

Corresponding PCT Application No. PCT/US2021/042286 International Search Report and Written Opinion dated Nov. 4, 2021.

What is UV-C Disinfection Lighting: The Basics' (Stouch Lighting Staff), Apr. 14, 2020 (Apr. 14, 2020), [online], retrieved from <URL:https://www.stouchlighting.com/blog/faqs-about-uv-disinfection-lighting-the-basics>, entire document.

* cited by examiner

1

SANITIZING HAIR DRYER

FIELD OF THE INVENTION

The present invention relates generally to devices for the care, treatment and enhancement of hair and, more particularly, to a hair dryer for styling, drying and enhancing hair.

BACKGROUND OF THE INVENTION

A hair dryer, also referred to as a blow dryer, is generally designed to emit a concentrated flow of heated air from a nozzle to quickly dry hair. Known hair dryers typically include a housing having a handle portion and a nozzle portion. A heating element mounted within the housing is configured to generate heat when supplied with electricity, while a fan driven by a motor within the housing draws outside air into the housing through a filter in the rear of the housing. As the air is forced across the heating element, it is heated, before being expelled out of the front of the nozzle portion.

Hair dryers are frequently used at home and in the professional setting at barber shops and hair salons. Salons and barber shops typically see a fairly large number of individuals in a confined space. Indeed, a salon worker using a hair dryer necessarily must come into close contact with the customer whose hair is being dried and/ or styled. It has been theorized that hair dryers have the potential to spread contaminated air around the room, particularly if the worker using the hair dryer is infected with germs such as bacteria and/or viruses (e.g., the worker may produce respiratory droplets in close proximity to the air intake of the hair dryer, which can be expelled at high velocity through the nozzle and directly towards the head of a customer).

The concern over the spread of contagions in hair salons and barber shops through the use of hair dryers has been heightened by the outbreak of COVID-19. Indeed, the year 2020 saw an unprecedented closure of businesses including barber shops and hair salons due, in part, to the concern over the potential spread of COVID-19 in hair salons, particularly through the use of hair dryers. Even as governing bodies relaxed social distancing guidelines and mandatory business closures, and permitted hair salons and barber shops to reopen, a number of such governing bodies mandated that hair dryers not be used.

In view of the above, there is a need for a hair dryer that is configured to minimize or inhibit the spread of contagions or germs during use.

SUMMARY OF THE INVENTION

It is an object of the present invention to provide a hair dryer.

It is another object of the present invention to provide a hair dryer emitting configured to minimize or inhibit the spread of contagions or germs during use.

It is another object of the present invention to provide a hair dryer having a light emitting element configured to deactivate or kill viruses and/or bacteria such as influenza and/or COVID-19 in air passing through the hair dryer.

It is another object of the present invention to provide a hair dryer having an ultraviolet light emitting element.

It is another object of the present invention to provide a hair dryer that provides a visual indication that the ultraviolet light emitting element is activated.

These and other objects are achieved by the present invention.

According to an embodiment of the invention, a hair dryer includes a housing having a handle portion and a nozzle portion, a motor within the housing, a fan drivingly connected to the motor within the housing, a heating element within the housing, and at least one ultraviolet light emitting element within the nozzle portion, the at least one ultraviolet light emitting element being configured to irradiate a flow passage of the nozzle portion with ultraviolet light. At least a portion of the housing adjacent to the at least one ultraviolet light emitting element is transparent or translucent allowing the ultraviolet light to be viewed from exterior to the housing.

According to another embodiment of the invention, a method of sanitizing a flow of air within a hair dryer having a housing having a handle portion and a nozzle portion, a motor within the housing, a fan drivingly connected to the motor within the housing, and at least one ultraviolet light emitting element within the nozzle portion is provided. The method includes the step of illuminating a flow passage within the nozzle portion with the at least one ultraviolet light emitting element, wherein light from the at least one light emitting element is viewable through a transparent or translucent area of the housing.

According to yet another embodiment of the invention, a hair dryer includes a housing having a handle portion and a nozzle portion, a motor within the housing, a fan drivingly connected to the motor within the housing, and a plurality of light emitting diodes associated with the nozzle portion, the plurality of light emitting diodes each being configured to irradiate a flow passage of the nozzle portion with ultraviolet light. The plurality of light emitting diodes are arranged in at least one of an annular array and a linear array.

BRIEF DESCRIPTION OF THE DRAWINGS

The present invention will be better understood from reading the following description of non-limiting embodiments, with reference to the attached drawings, wherein below.

DETAILED DESCRIPTION OF THE PREFERRED EMBODIMENT

Figure 1:
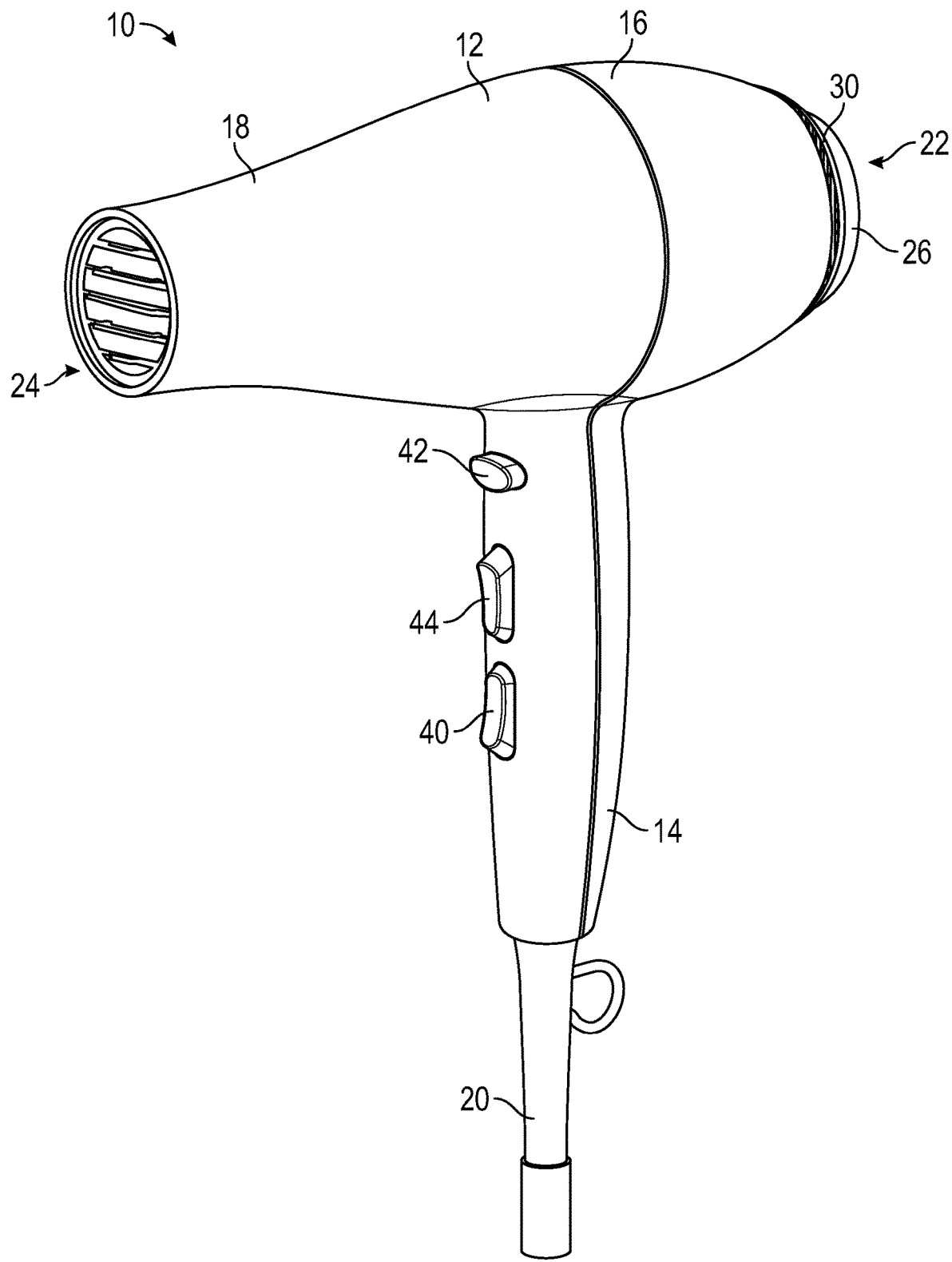
FIG. 1 is a front, perspective view of a hair dryer according to an embodiment of the present invention.
Figure 2:
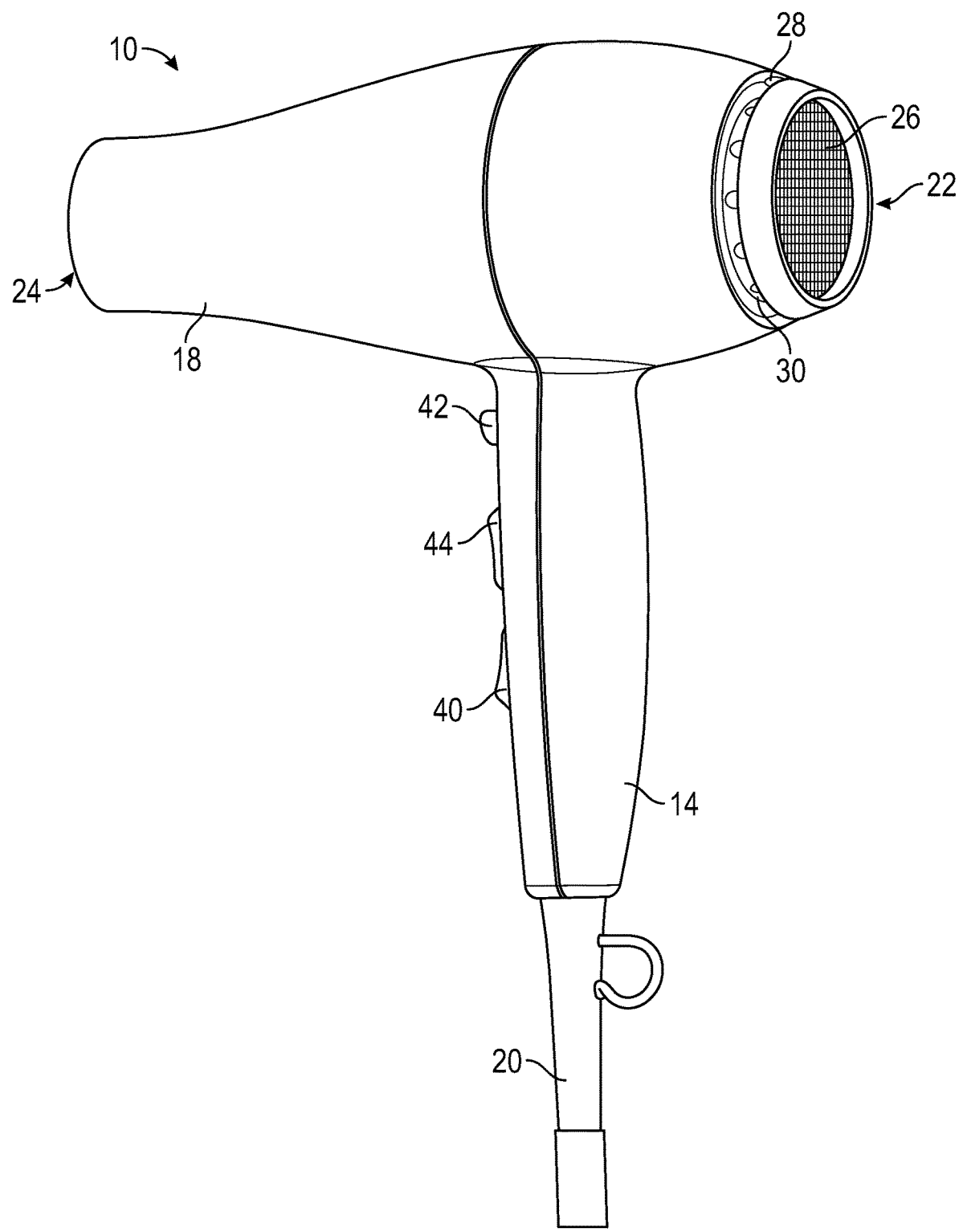
FIG. 2 is a rear, perspective view of the hair dryer of FIG. 1.
Figure 3:
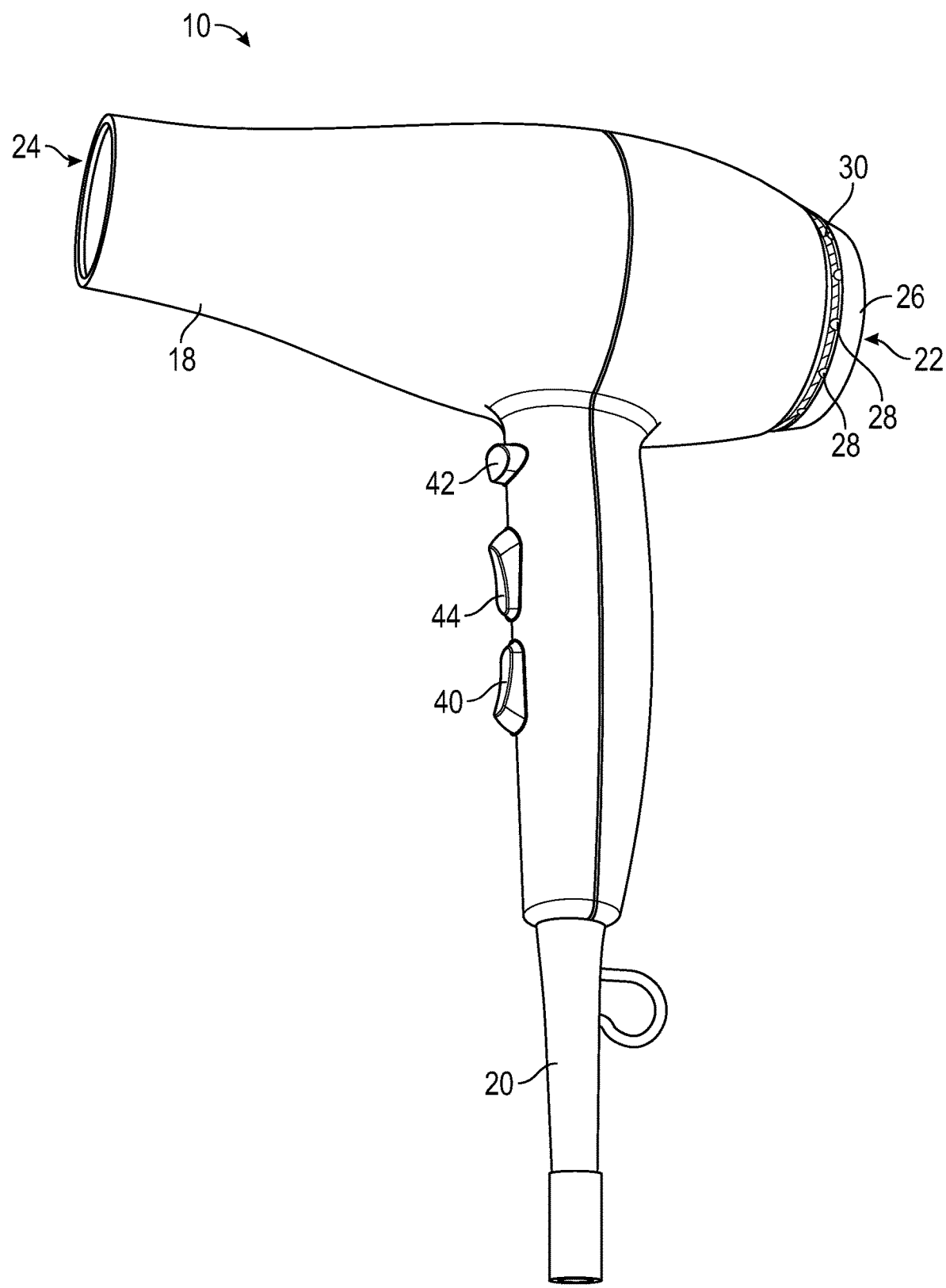
FIG. 3 is a bottom, perspective view of the hair dryer of FIG. 1.
Figure 4:
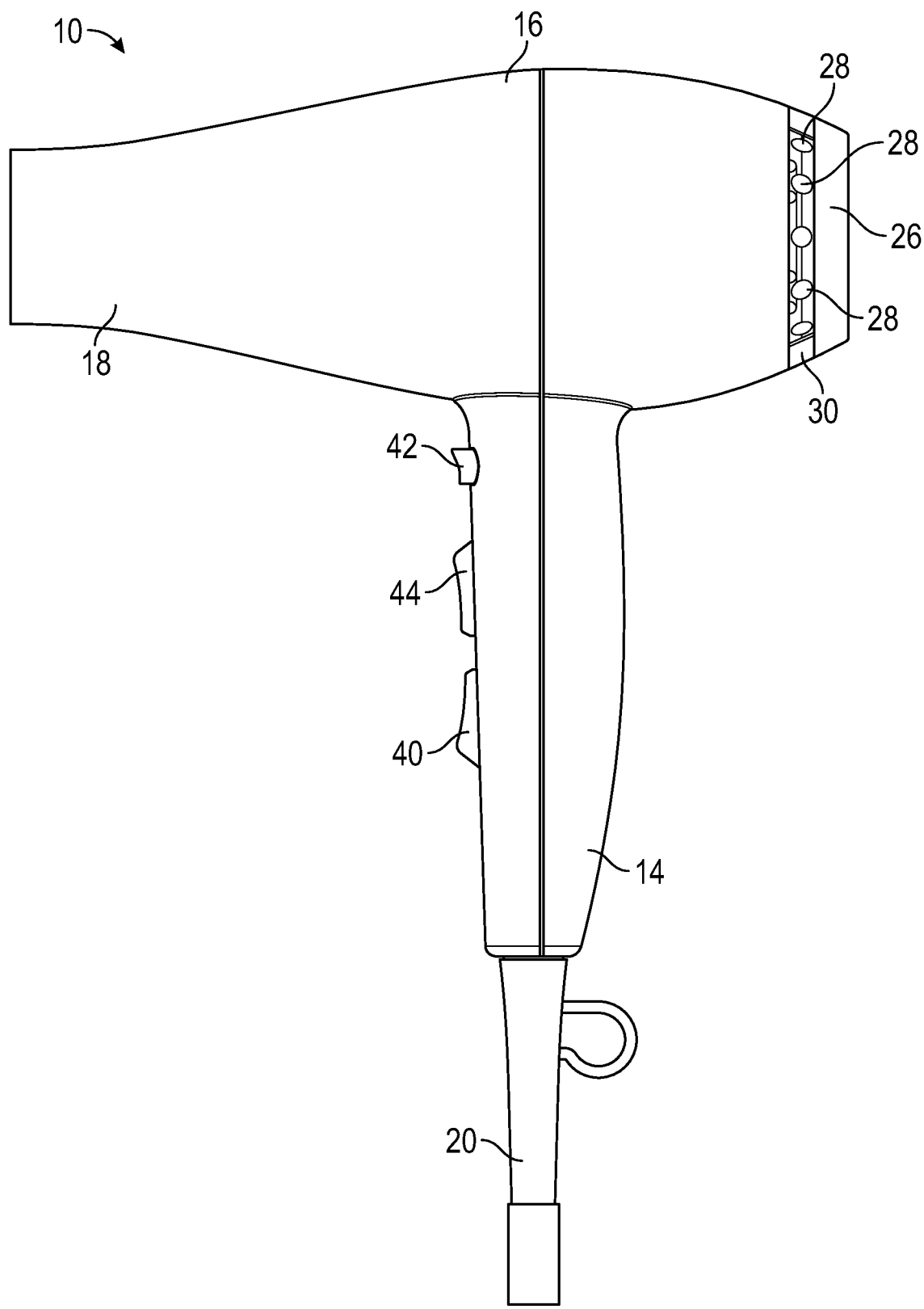
FIG. 4 is a side elevational view of the hair dryer of FIG. 1.

With reference to FIGS. 1-6, a hair dryer 10 according to an embodiment of the present invention is illustrated. The hair dryer 10 is illustrated as a hand-held, electrically powered hair dryer 10 embodying aspects of the invention as disclosed herein. The hair dryer 10 includes a housing 12 having a handle portion 14, a head portion 16 connected to an upper end of the handle portion 14, and a nozzle or barrel 18 connected to or otherwise forming a part of, and extending from, the head portion 16. The head portion 16 and nozzle 18 may collectively be referred to as the nozzle portion. As shown therein, the handle 14 is generally elongate, and the nozzle 18 extends generally perpendicularly from the handle. In an embodiment, a diffuser or concentrator (not shown) may be removably attached to the nozzle 18 and configured to further concentrate airflow emitted from the hair dryer 10. A power supply or power cord 20 is connected to the distal, lower end of the handle 14 to provide electricity to the hair dryer 10. The power cord 20 is configured to engage a suitable electrical outlet (e.g., a wall outlet, etc.). However, in other embodiments, any suitable source of electricity may be incorporated into the hair dryer 10, including, but not limited to a battery or rechargeable battery.

As further shown therein, housing 12 includes an air inlet 22 associated with the rear end of the nozzle 18, and an air outlet 24 associated with the forward end of the nozzle 18. In an embodiment, the air inlet 22 may take the form of a filter cap 26 mounted to the rear end of the housing 12 forming or retaining a filter for preventing lint, debris and other particles or objects from entering the housing through the inlet 22. The filter cap 26 may be a unitary part with the housing 12 or may be a separate part that is removable from the rear of the housing 12.

As further shown in FIGS. 1-6, in an embodiment, the hair dryer 10 includes at least one, and preferably a plurality of, light emitting elements 28 positioned within the housing 12 in longitudinal alignment with a transparent or translucent ring 30 that forms a part of, or is otherwise receivable by, the housing 12. In particular, the transparent ring 30 is positioned adjacent to the rear end of the housing 12, just forward of the filter cap 26, and the light emitting elements 28 are positioned just inside the ring 30. As described herein, the ring 30 and filter cap 26 may be considered to be part of the housing 16, such that at least a portion of the housing 16 is transparent, allowing for viewing of the light emitting elements 28 within the housing 16, as discussed hereinafter. In an embodiment, the light emitting elements 28 are mounted to, or otherwise retained by, the ring 30. In other embodiments, the light emitting elements 28 may be a separate component from the ring 30 (e.g., the light emitting elements 28 may be mounted on a separate ring-shaped strip or separately mounted within the housing 16).

In an embodiment the light emitting elements 28 are ultraviolet light emitting diodes (UV LEDs) and are positioned in an annular array interior to the transparent ring 30. The light emitting elements 28 are configured and positioned so as to irradiate the flow passageway within the housing 18, as described below. For example, in an embodiment, the UV LEDs 28 are angled so that the light emitted is directed toward a longitudinal axis of the nozzle 18. In an embodiment, the annular array may extend between about 180 degrees and about 360 degrees and, more preferably, between about 300 degrees and 360 degrees.

Figure 5:
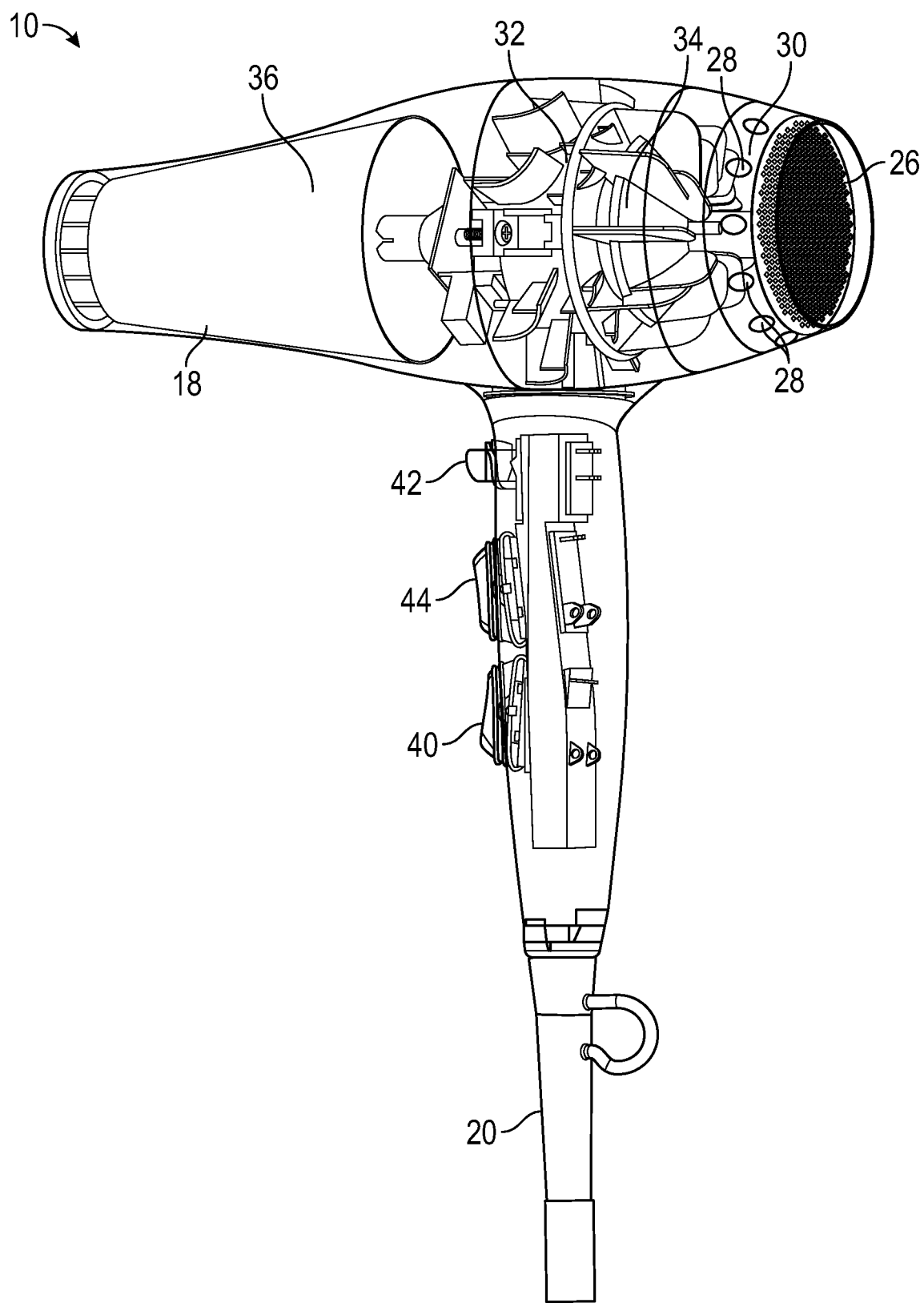
FIG. 5 a transparent, perspective view of the hair dryer of FIG. 1, illustrating the internal components thereof.
Figure 6:
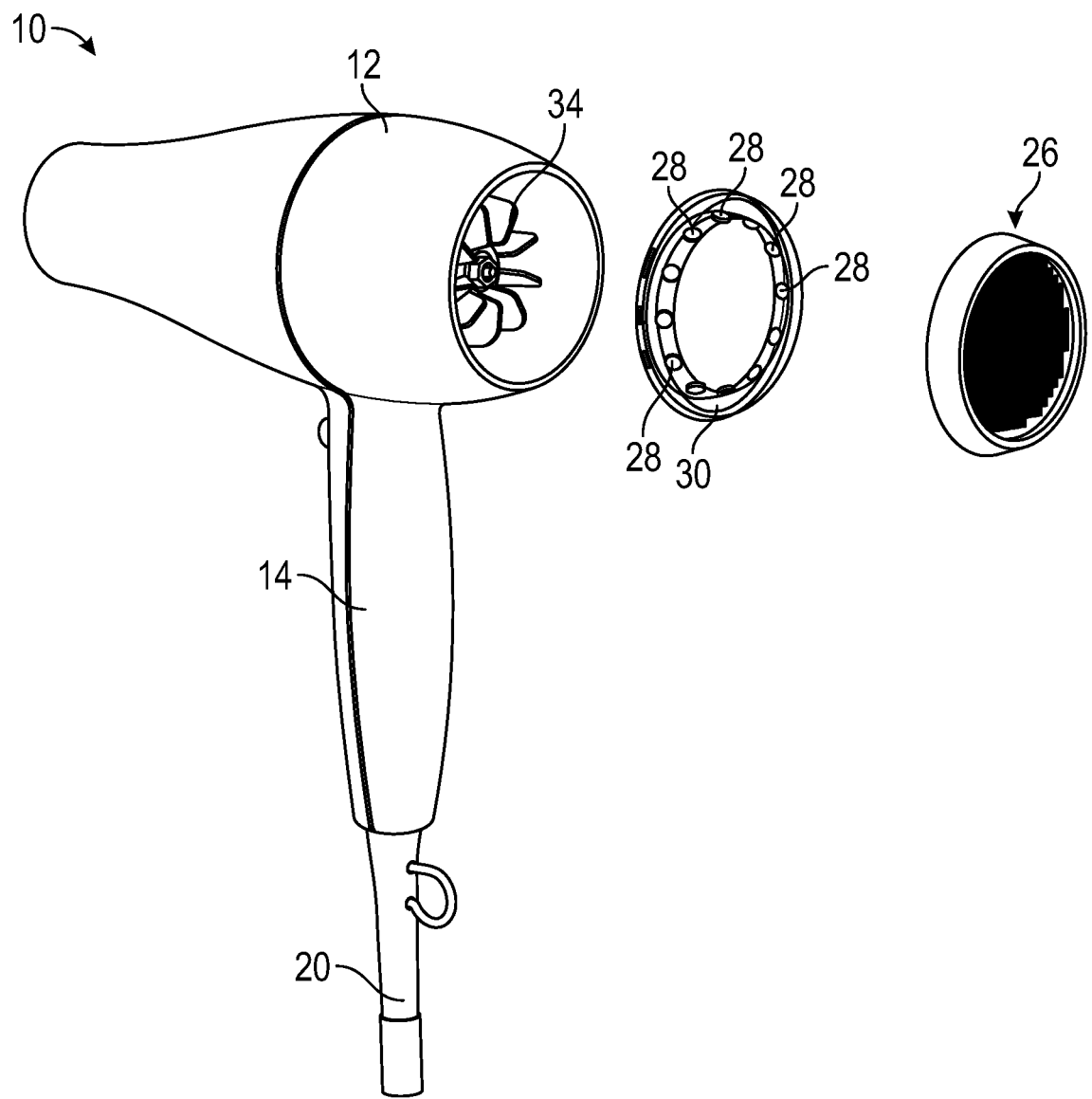
FIG. 6 an exploded, rear perspective view of the hair dryer of FIG. 1.

As best shown in FIG. 5, the hair dryer 10 further includes a motor 32 and a fan 34 drivingly connected to the motor 32 within the housing 12. In operation, air is drawn into the hair dryer 10 through the air inlet 22 via operation of the fan 34, where it is concentrated, optionally heated, and emitted through the air outlet 24 in a manner known in the art. For example, the hair dryer 12 may also include a heating element 36 for heating the air as it passes through the nozzle 18. In an embodiment, the heating element may be a coiled nichrome wire wrapped around insulating mica boards positioned within the nozzle 18, although other heating elements/mechanisms known in the art may also be utilized without departing from the broader aspects of the invention.

The motor 32, fan 34, heating element 36 and light emitting elements 28 are electrically connected to the power cord 20 so as to receive a supply of electrical power therefrom. As shown in FIGS. 1-6, the hair dryer 10 further includes a control interface on the forward side of the handle portion 14 having a plurality of buttons or switches for controlling operation of the hair dryer 10. For example, in an embodiment, a first switch 40 may activate the heating element and motor 32 (and fan 34) to deliver a flow of heated air from the outlet 24. In some embodiments, this switch 40 may have various positions corresponding to various fan speeds. The hair dryer 10 may also include a button 42 that deactivates the heating element 36 when depressed, so as to provide for the flow of cool air only out of the outlet 24. In addition, a second switch 44 may control activation/energization (and deactivation) of the light emitting elements 28. While it is disclosed that the light emitting element2 28 and operation of the heating elements and fan to deliver a flow of heated air are separately operable, in other embodiments, the light emitting elements 28, heating element 36, motor 32 (and fan 34) may be electrically connected to a single switch so that any time the switch is actuated to deliver a flow of air out of the outlet 24, the light emitting elements 28 are also activated/illuminated. In an embodiment, the switches 26, 28 may be configured as rocker or sliding switches, although other switch configurations or type known in the art may also be utilized without departing from the broader aspects of the invention.

As indicated above, the light emitting elements 28 are preferably UV LEDs configured to irradiate the air passing thereby. As also disclosed above, these UV LEDs 28 are arranged in a ring and are positioned just forward of the filter cap 26/air intake (between the filter cap 26 and the fan 34). Importantly, the UV LEDs 28 are angled so that they are not directly viewable if looking through the inlet 22 or outlet 24 (i.e., they are not capable of transmitting a direct beam to the eyes of a person looking into the inlet 22 or outlet 24). The transparent portion of the housing 16 (e.g., the transparent ring 30), however, allows the glow from the UV LEDs 28 to be seen by a user, providing a visual indication that the UV LEDs are energized and working to irradiate the flow of air passing through the housing 16. In an embodiment, the transparent portion of the housing (e.g., the ring 30) is formed from a material that absorbs UV radiation so that a user can view the UV LEDs without being subjected to UV radiation. For example, in an embodiment, the transparent ring 30 may be formed from glass, plastic or other material such as, for example, ANSI Z87 rated glass or plastic.

In use, the UV LEDs may sanitize the internal components of the hair dryer 10 and, more importantly, sanitize the air passing through the hair dryer 10 before it exits through the outlet 24. In an embodiment, the UV LEDs 28 may emit light having wavelengths ranging from about 100 nanometers to about 415 nanometers. In particular, in an embodiment, the UV LEDs may emit light in at least one of the UV-A (about 315 to about 415 nanometers), UV-B (about 280 to about 315 nanometers) and/or UV-C (about 100 to about 280 nanometer) ranges. Preferably, the UV LEDs emit light having wavelengths ranging from about 100 nanometers to about 280 nanometers (i.e., UV-C), which has been shown to kill bacteria and inactivate viruses such as, for example, COVID-19 and influenza.

The UV LEDs 28 may emit light continuously, in regular pulses, or in irregular pulses. In an embodiment, the intensity of the UV LEDs 28 may be sufficient to kill bacteria, mold, yeast, fungi, and certain viruses entrained in the airflow passing through the housing 16 and on internal components within the housing 16. The hair dryer 10 of the invention, therefore, functions to disinfect air moving into and out of the hair dryer during use and therefore, to some degree, improves the cleanliness of the air being blown onto a user during use as well as the surrounding air. As will be appreciated therefore, use of the hair dryer 10 of the invention inhibits the spread of bacteria and viruses, such as COVID-19, within hair salons, barber shops and similar settings to a degree heretofore not possible with the use of conventional hair dryers.

Figure 7:
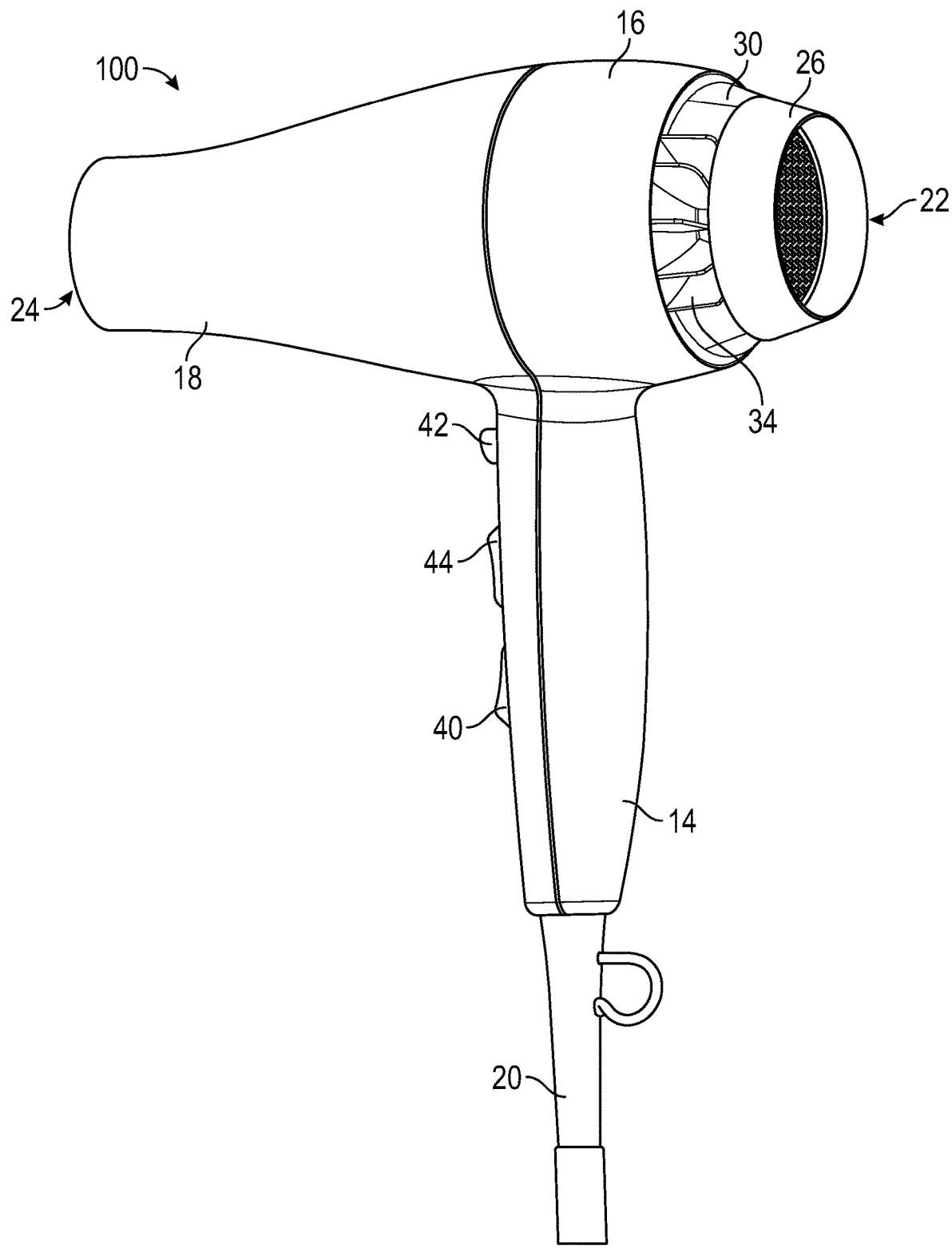
FIG. 7 is a rear perspective view of a hair dryer according to another embodiment of the invention, showing an alternative configuration of ultraviolet LEDs.
Figure 8:
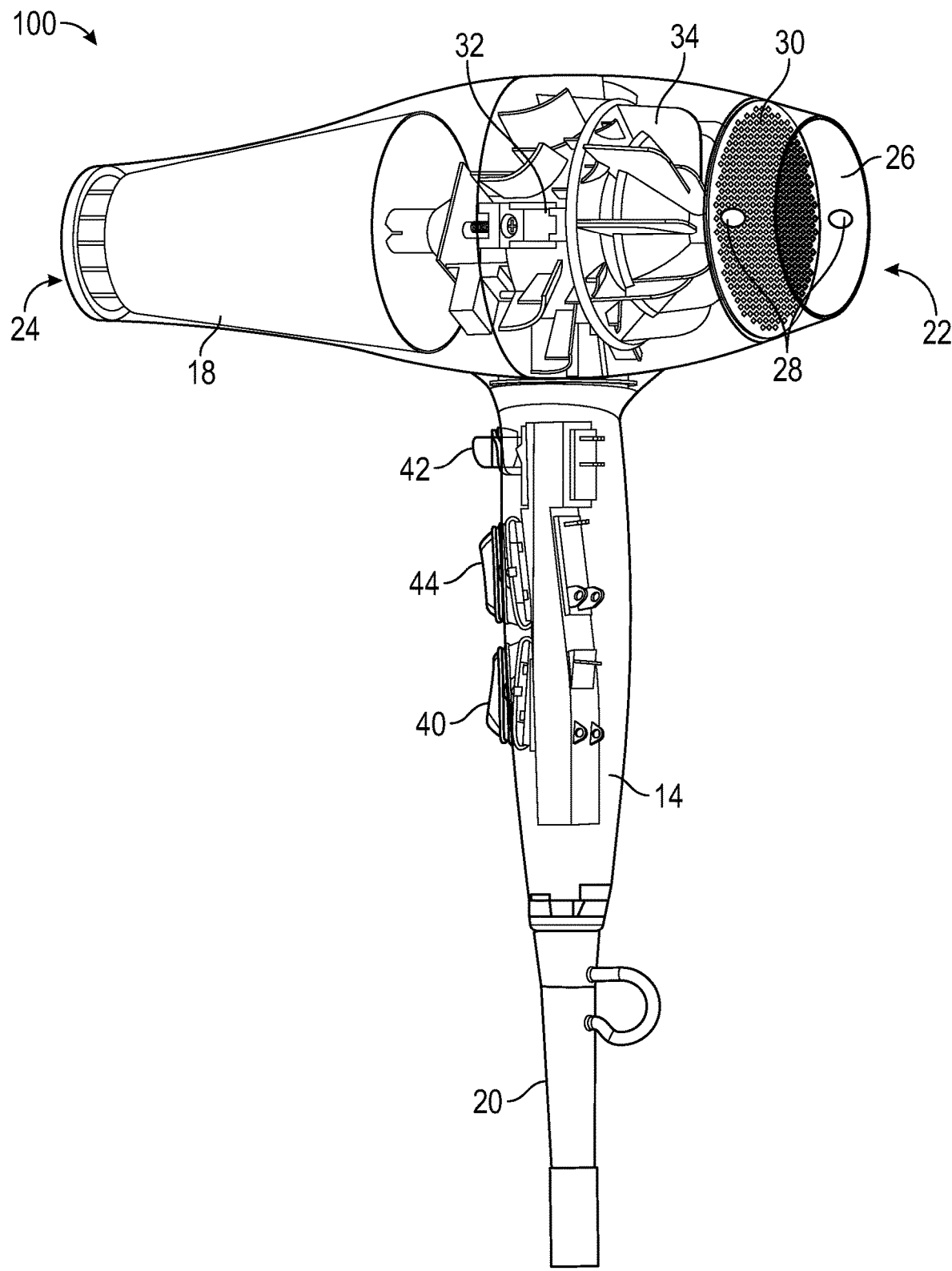
FIG. 8 is a transparent, perspective view of the hair dryer of FIG. 7.
Figure 9:
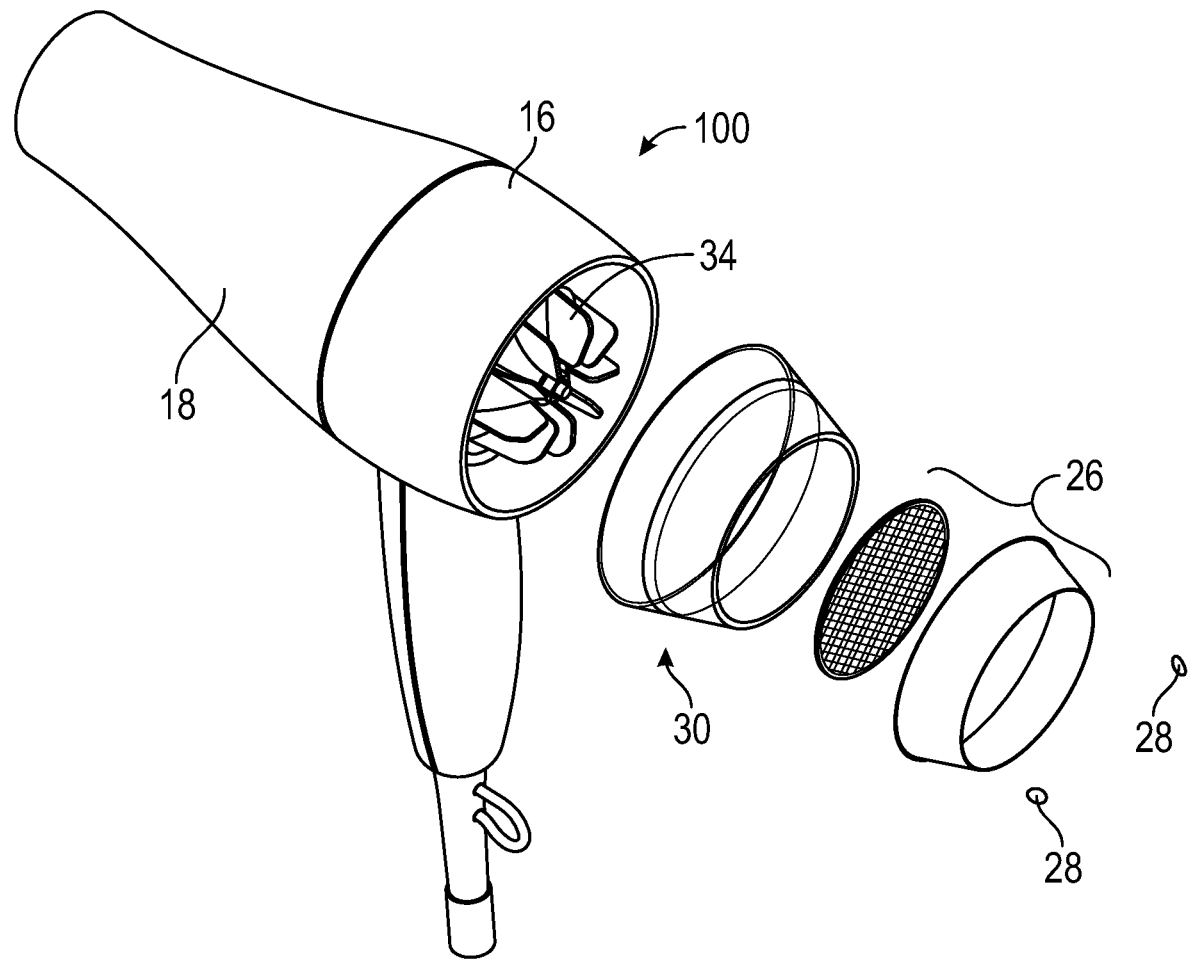
FIG. 9 is an exploded, rear perspective view of the hair dryer of FIG. 7.
Figure 10:
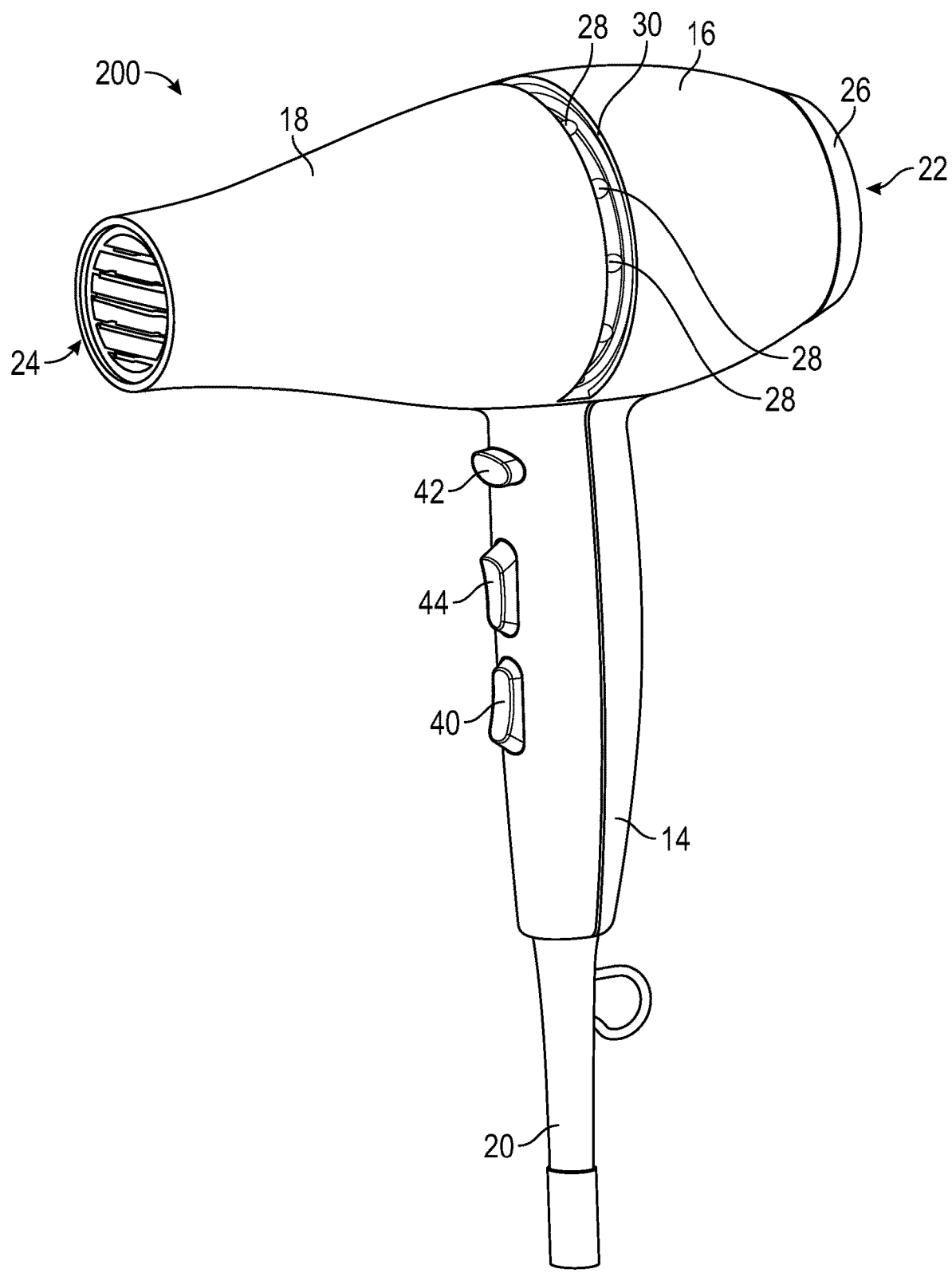
FIG. 10 is a front, perspective view of a hair dryer according to another embodiment of the present invention.
Figure 11:
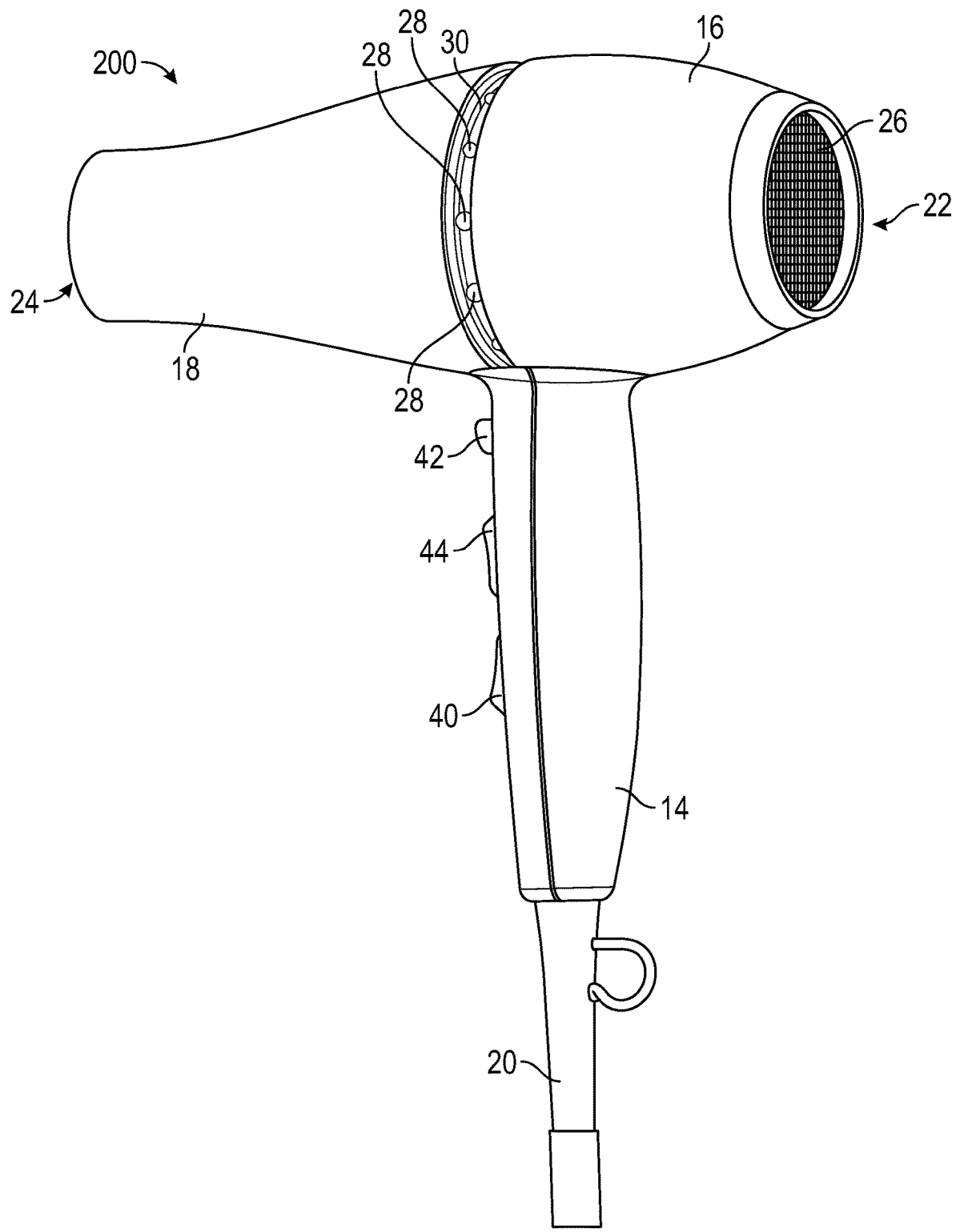
FIG. 11 is a rear, perspective view of the hair dryer of FIG. 10.
Figure 12:
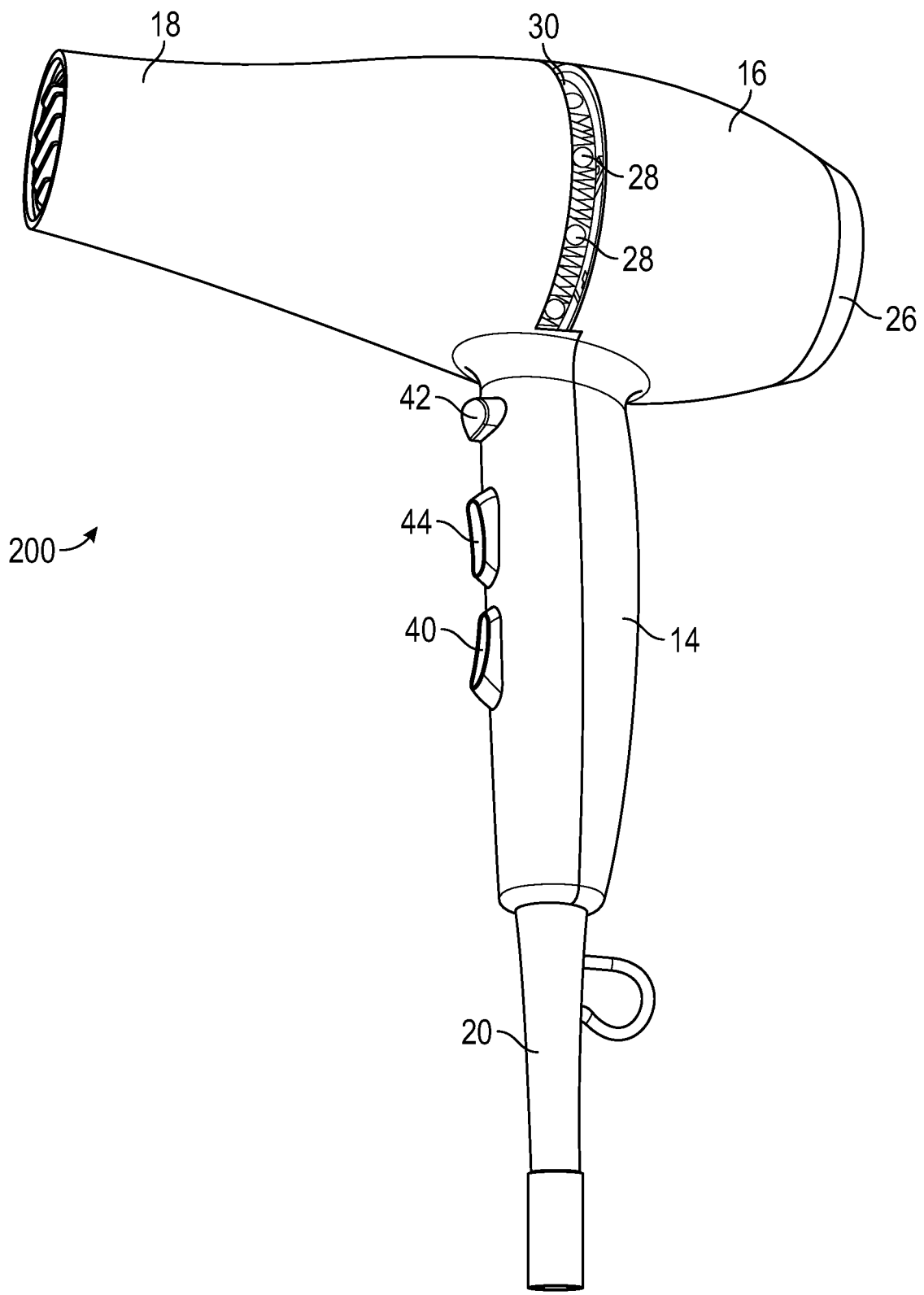
FIG. 12 is a bottom, perspective view of the hair dryer of FIG. 10.
Figure 13:
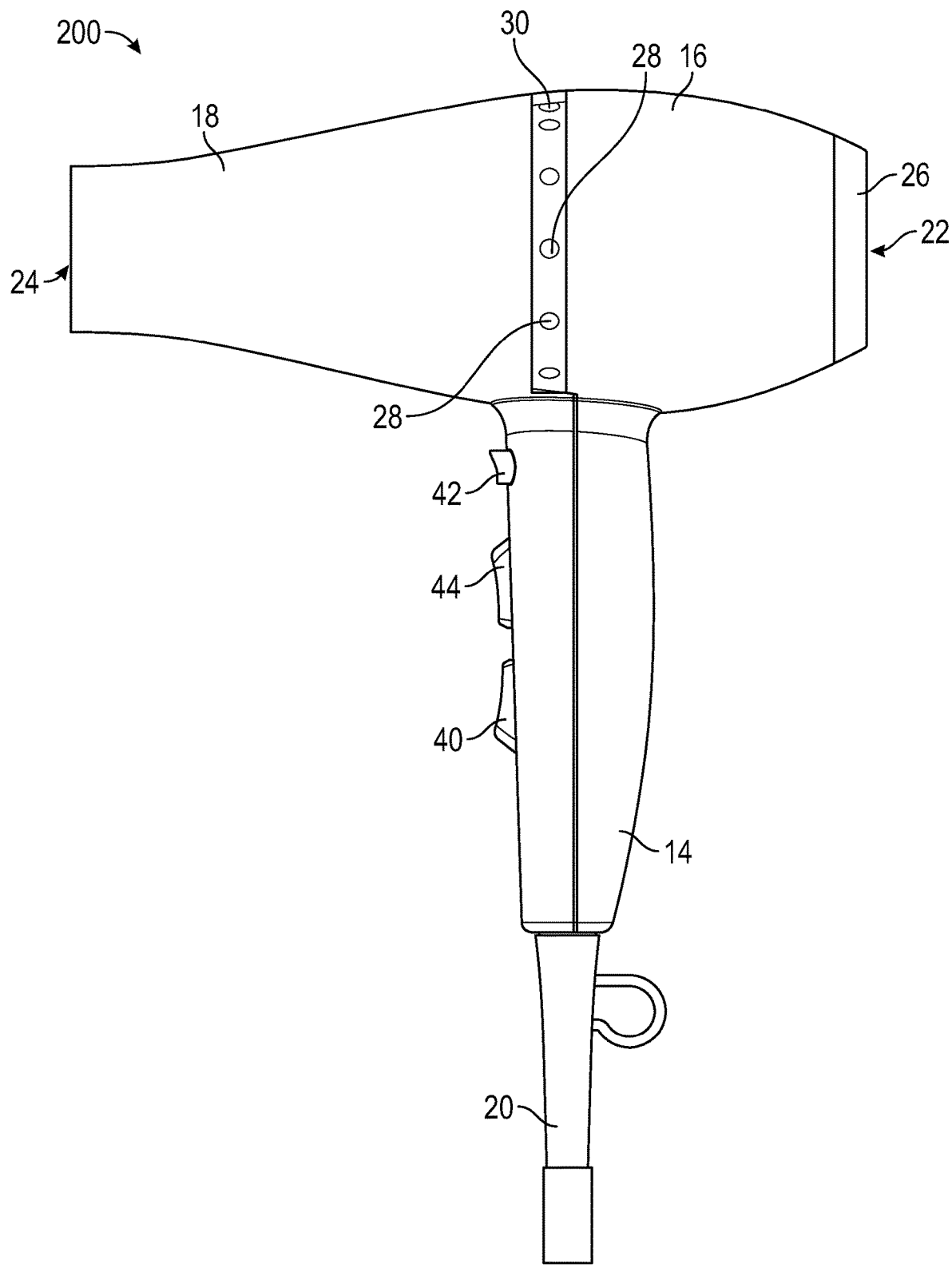
FIG. 13 is a side elevational view of the hair dryer of FIG. 10.

Turning now to FIGS. 7-9, a hair dryer 10 according to another embodiment of the present invention is illustrated. The hair dryer 100 is substantially similar to the hair dryer 10, where like reference numerals designate like parts. Rather than the UV LEDs 28 being arranged in an annulus, however, the hair dryer 100 has UV LEDs 28 located on opposing sides of the housing 16 in front of the rear filter/filter cap 26. As shown therein, for example, the hair dryer 100 may have a pair of UV LEDs positioned on the left and right sides of the housing 16.

Figure 14:
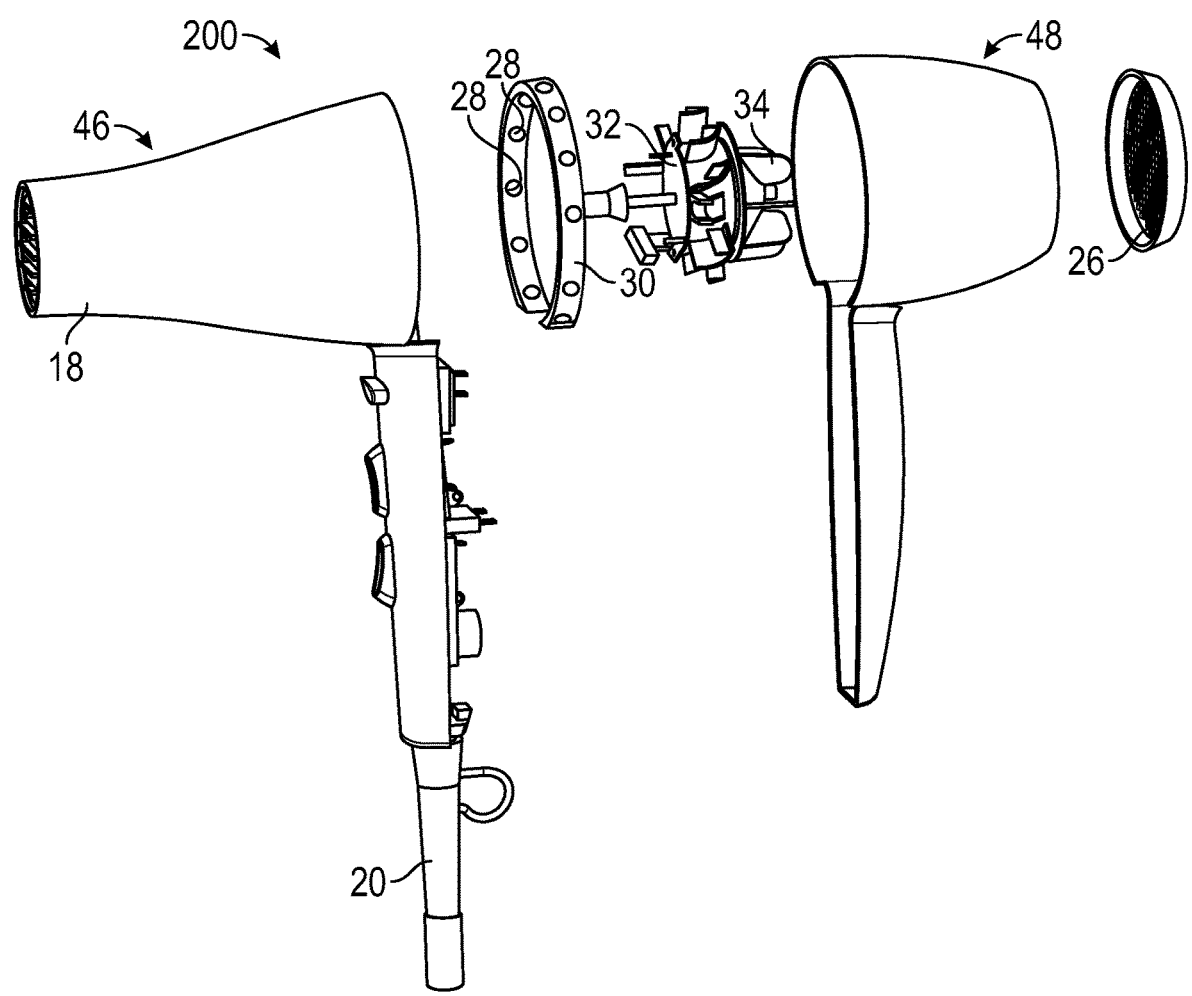
FIG. 14 an exploded view of the hair dryer of FIG. 10.

With reference to FIGS. 10-14, a hair dryer 200 according to another embodiment of the present invention is illustrated. As shown therein, the hair dryer 200 is substantially similar to the hair dryer 10, where like reference numerals designate like parts. Rather than the UV LEDs 28 being positioned/located rearward of the fan 34 adjacent to the filter of the end cap 26, however, the UV LEDs are arrayed in a ring shape and positioned forward of the fan 34 at a general midpoint of the housing 16. The transparent portion of the housing 16 (i.e., the transparent ring 30) is also positioned forward of the fan 34 in longitudinal alignment with the UV LEDs so that a user can see the emitted light through the ring 30. As best shown in FIG. 14, the transparent ring 30 may be sandwiched between front and rear portions 46, 48 of the housing 16, which may aid in assembly and manufacturing.

As with the hair dryer 10, the UV LEDs of hair dryer 200 are configured to emit UV light toward the longitudinal axis of the nozzle 18, irradiating the air passing therethrough to sanitize the air (e.g., kill bacteria and inactivate viruses such as influenza and COVID -19). Importantly, as disclosed above, the UV LEDs are oriented and/or angled so that they are not directly viewable when looking through the inlet 22 or outlet 24. Moreover, the transparent ring 30, as disclosed above, is formed from a material that enables a user to see when the glow of the UV LEDs through the sides and top of the housing 16 when the UV LEDs are activated or energized, but blocks/absorbs radiation.

Figure 15:
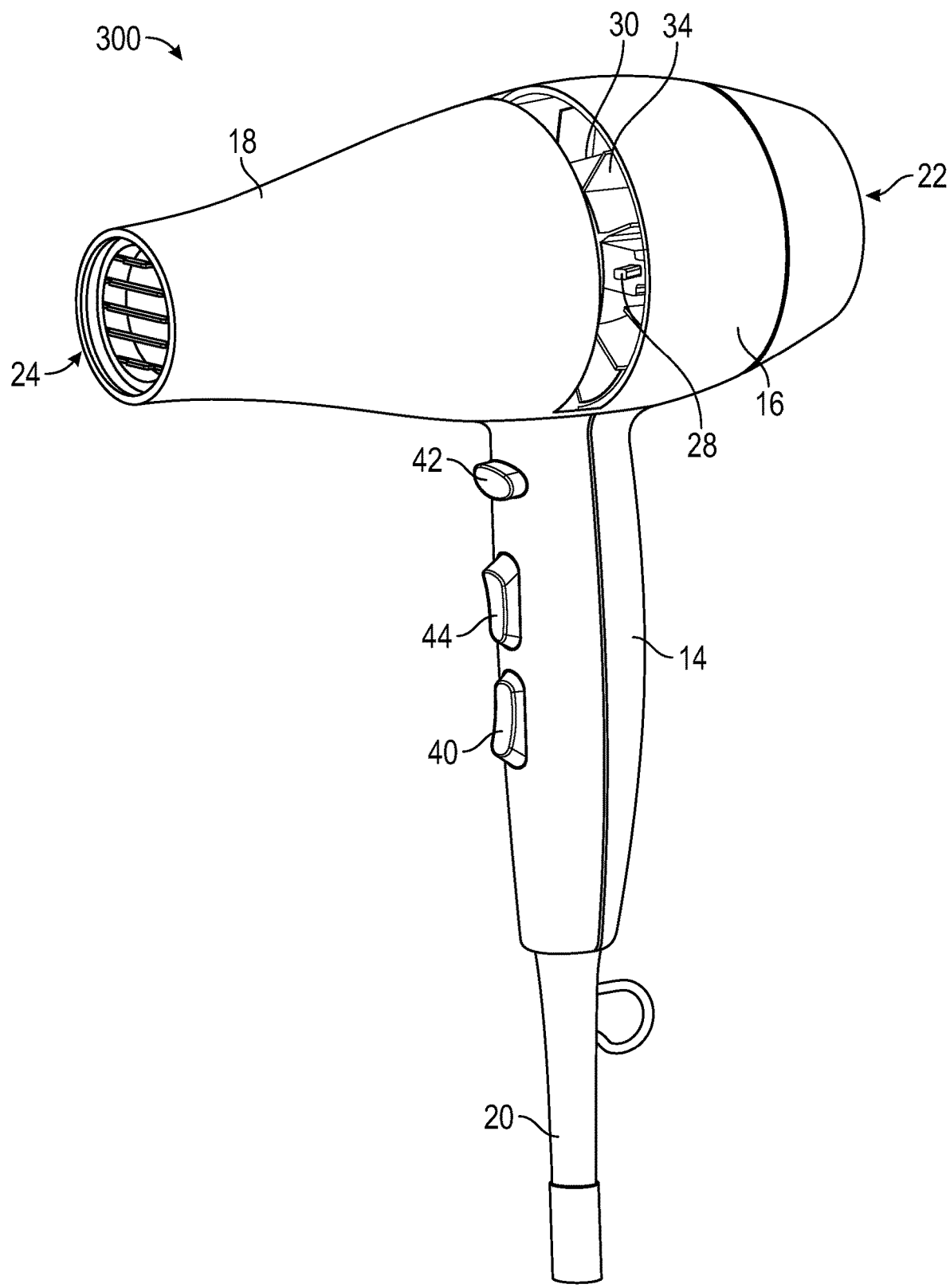
FIG. 15 is a front perspective view of a hair dryer according to another embodiment of the invention, showing an alternative configuration of ultraviolet LEDs.
Figure 16:
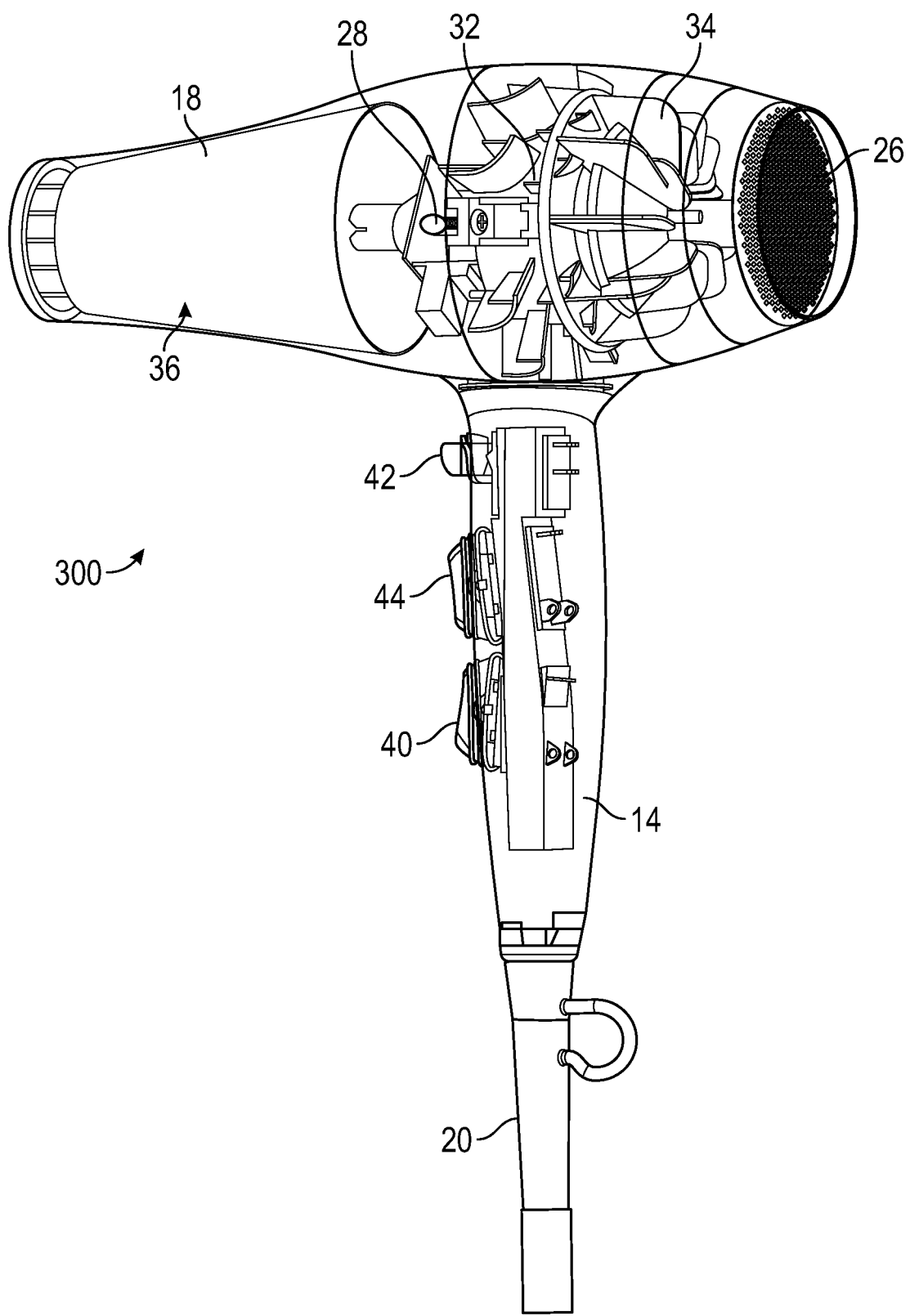
FIG. 16 is a transparent, perspective view of the hair dryer of FIG. 15, illustrating the internal components thereof.
Figure 17:
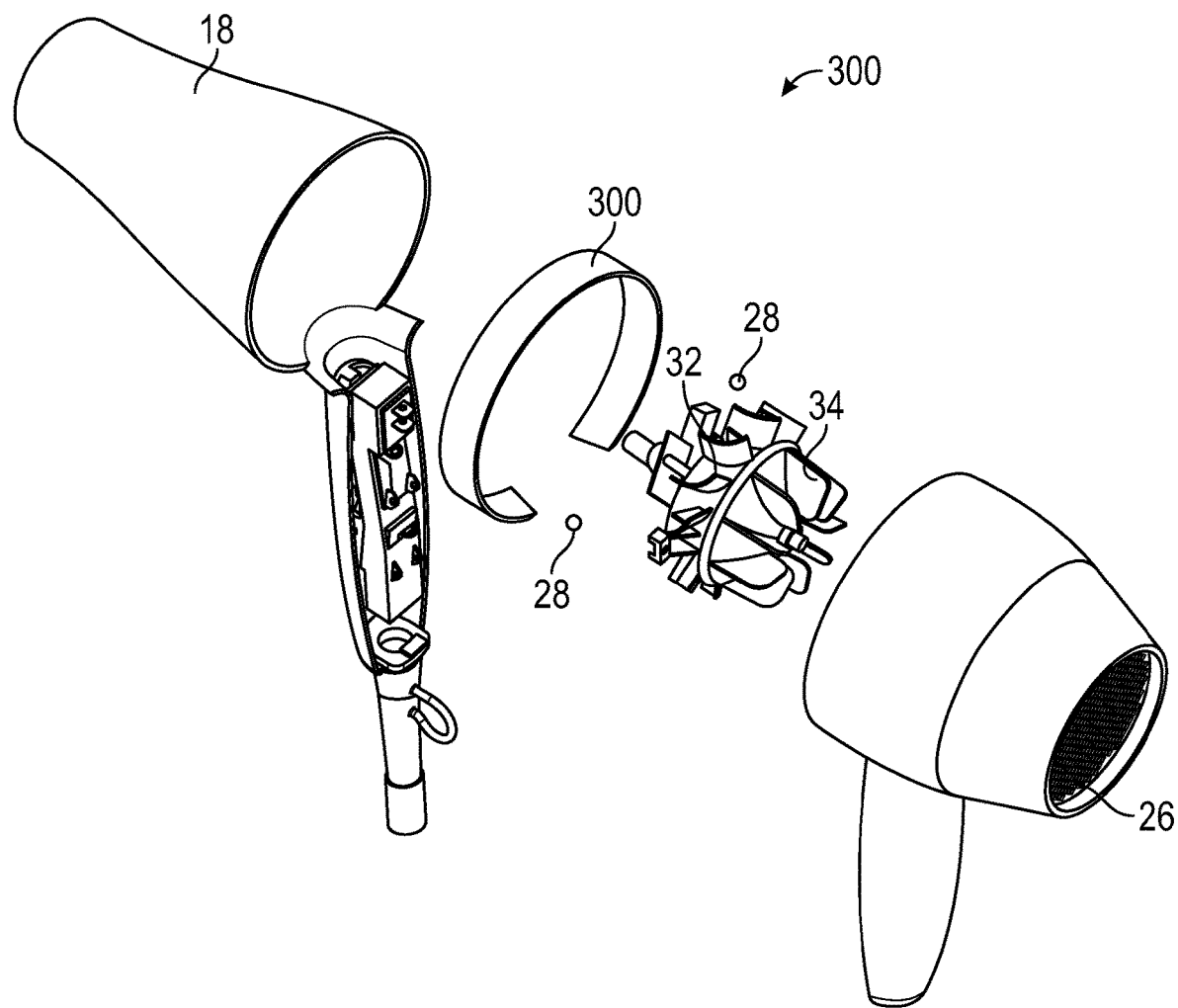
FIG. 17 is an exploded, rear perspective view of the hair dryer of FIG. 15.

Similar to the embodiment shown in FIGS. 7-9, in another embodiment, rather than the UV LEDs 28 being arranged in an annulus, however, a hair dryer 300 may have UV LEDs located on opposing sides of the housing 16 in front of the fan 34, as shown in FIGS. 15-17. As shown therein, for example, the hair dryer 300 may have a pair of UV LEDs 28 positioned on the left and right sides of the housing 16 at the general longitudinal midpoint thereof.

Figure 18:
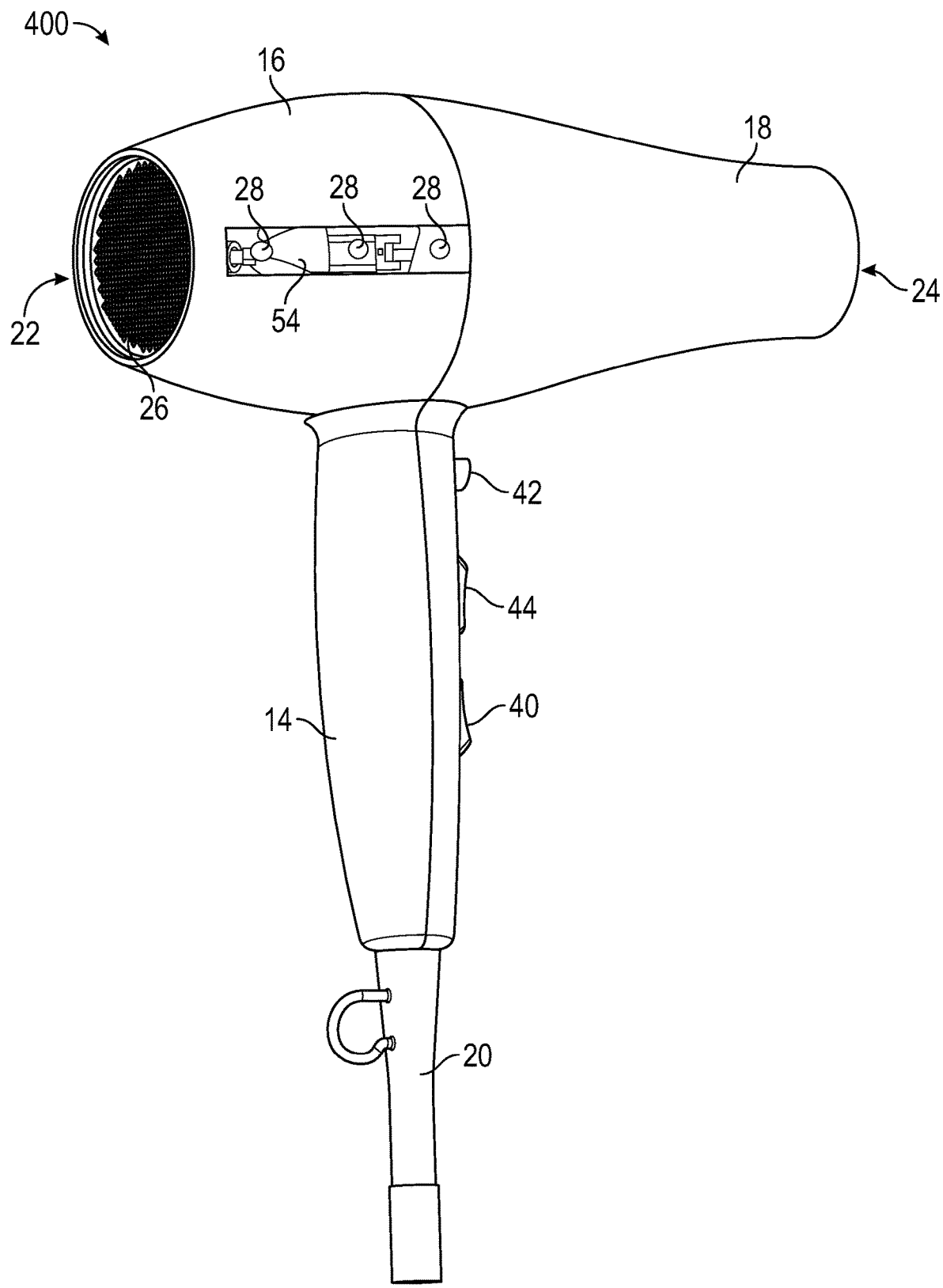
FIG. 18 is a rear perspective view of a hair dryer according to another embodiment of the present invention.
Figure 19:
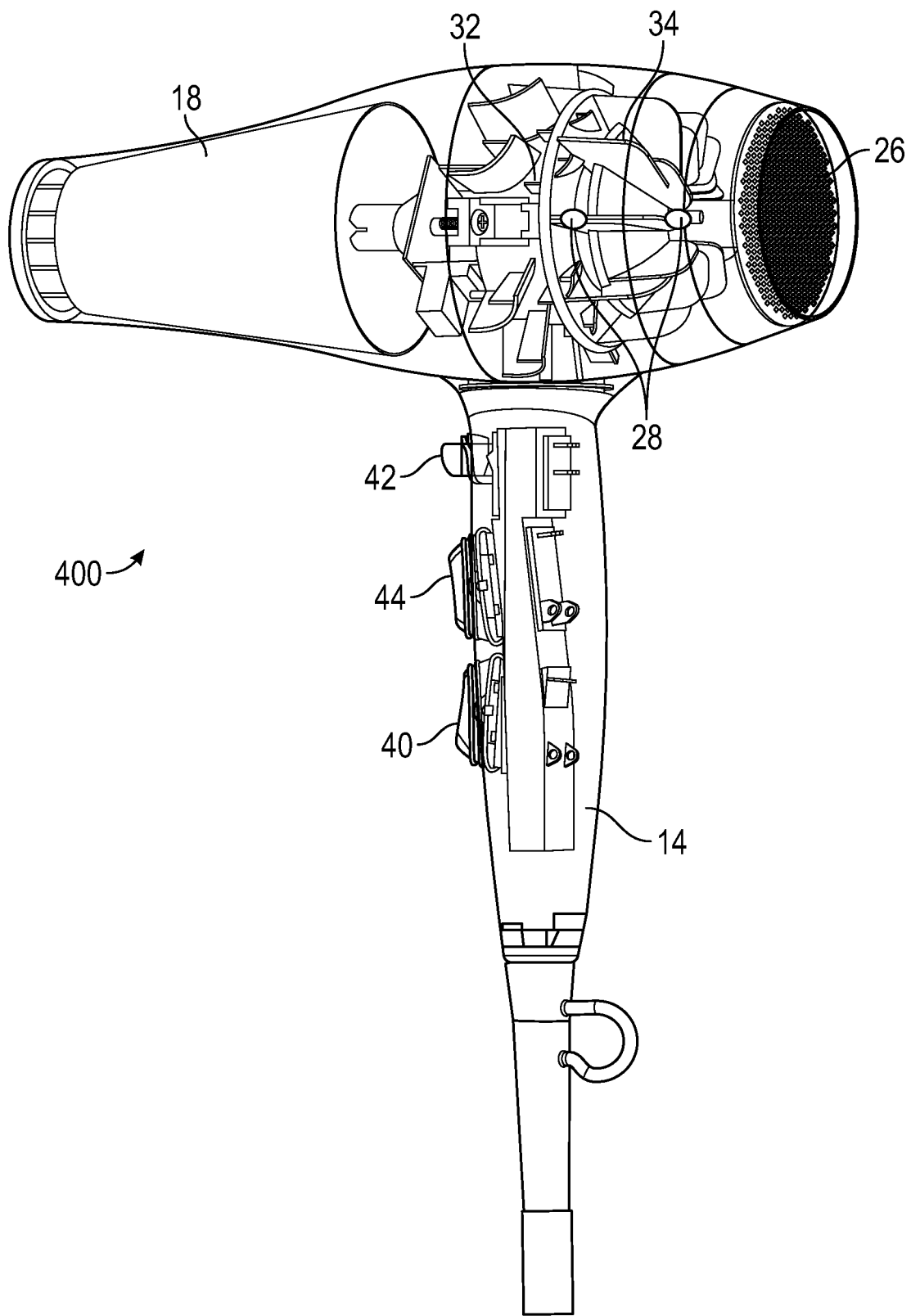
FIG. 19 is a transparent, perspective view of the hair dryer of FIG. 18, illustrating the internal components thereof.
Figure 20:
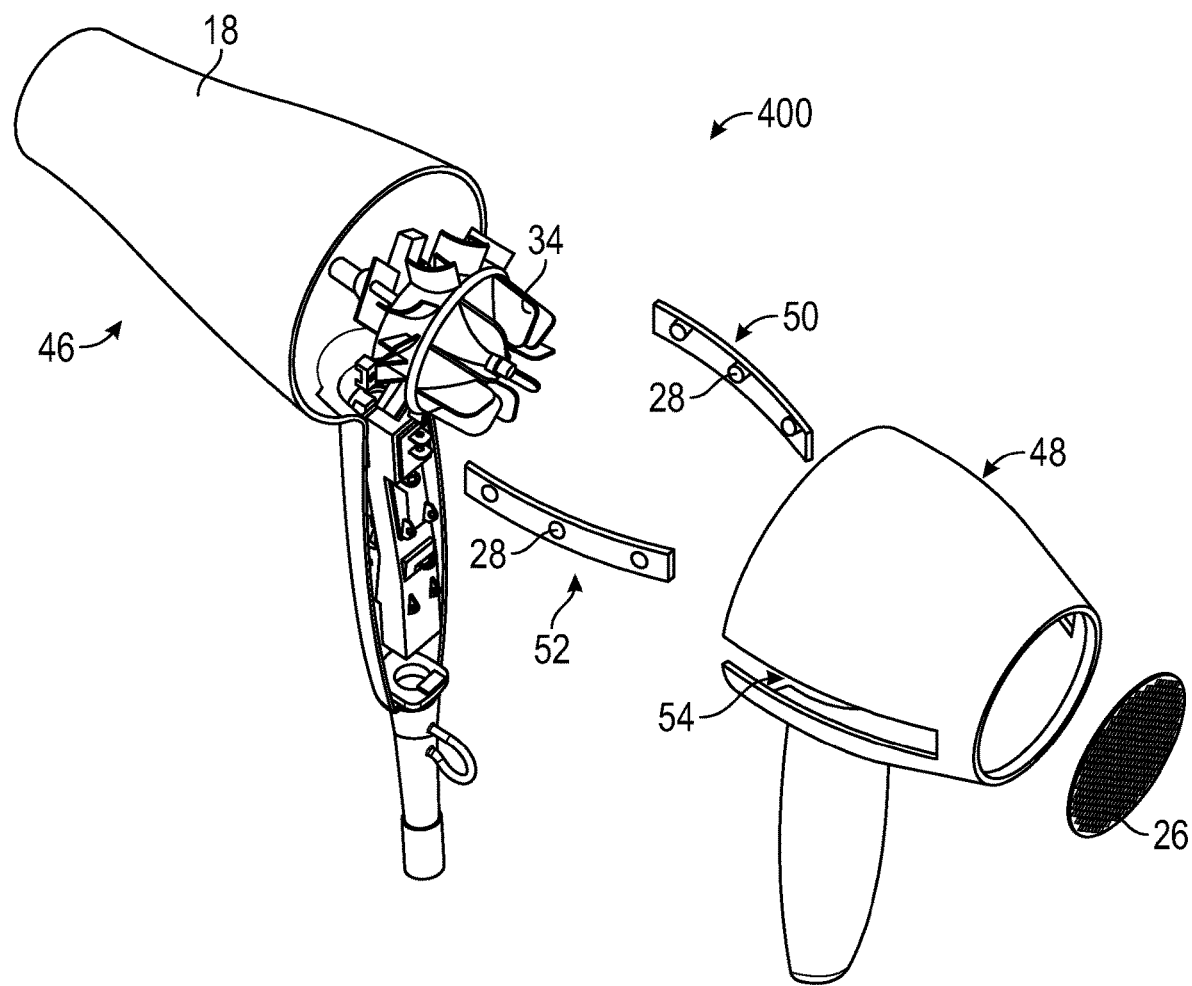
FIG. 20 is an exploded, rear perspective view of the hair dryer of FIG. 18.
Figure 21:
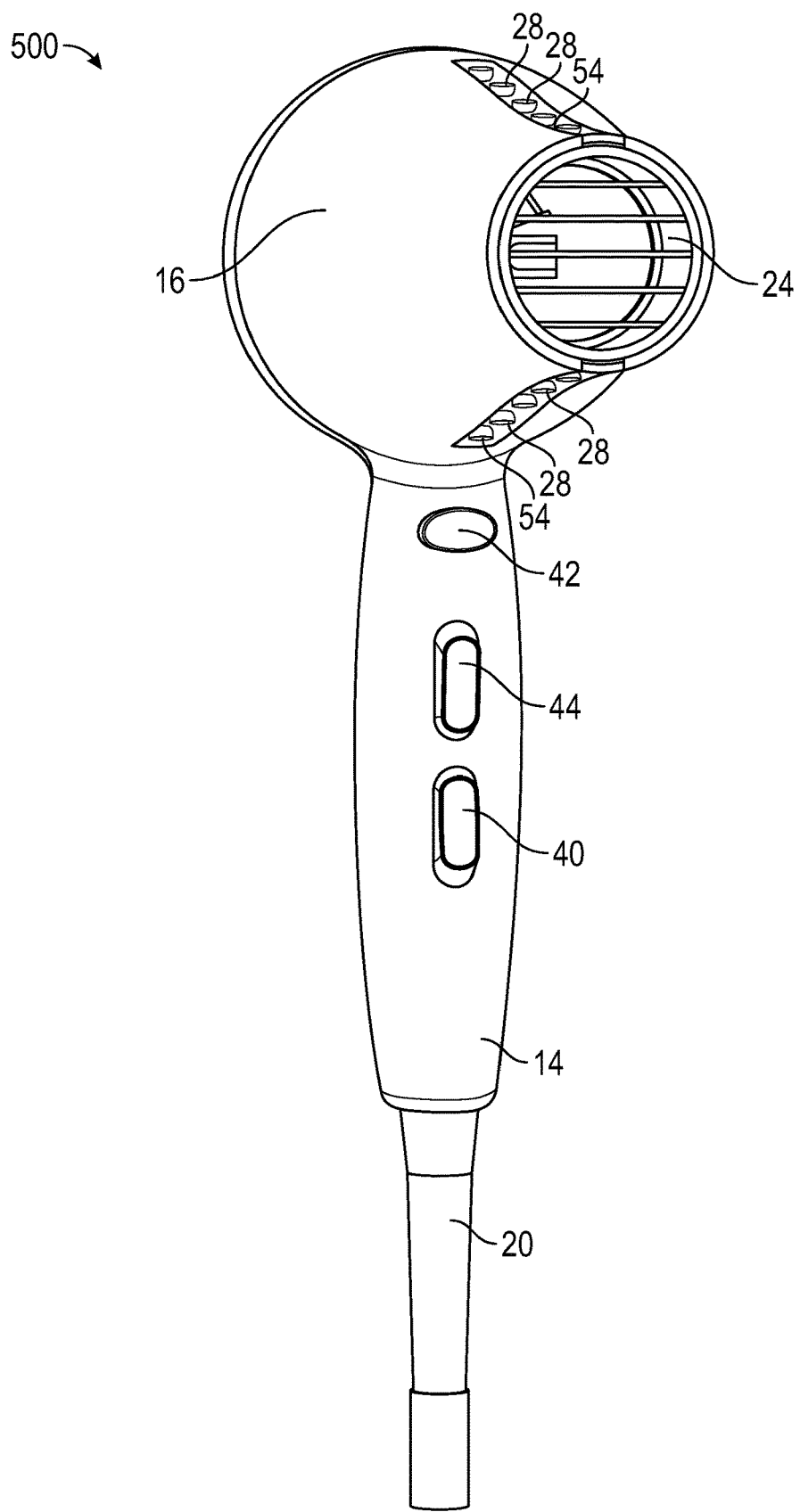
FIG. 21 is a front, perspective view of a hair dryer according to another embodiment of the present invention.
Figure 22:
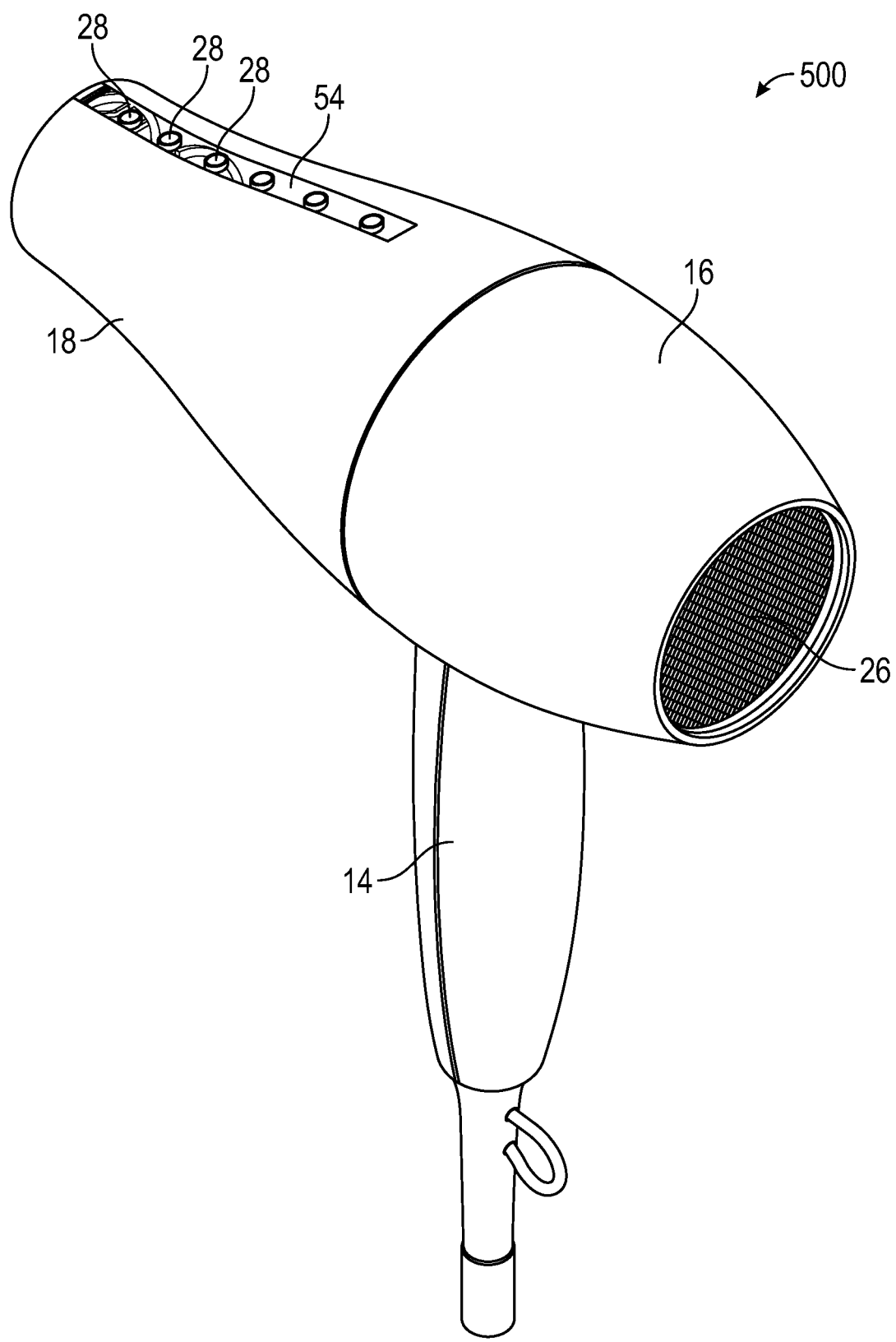
FIG. 22 is a rear, perspective view of the hair dryer of FIG. 21.
Figure 23:
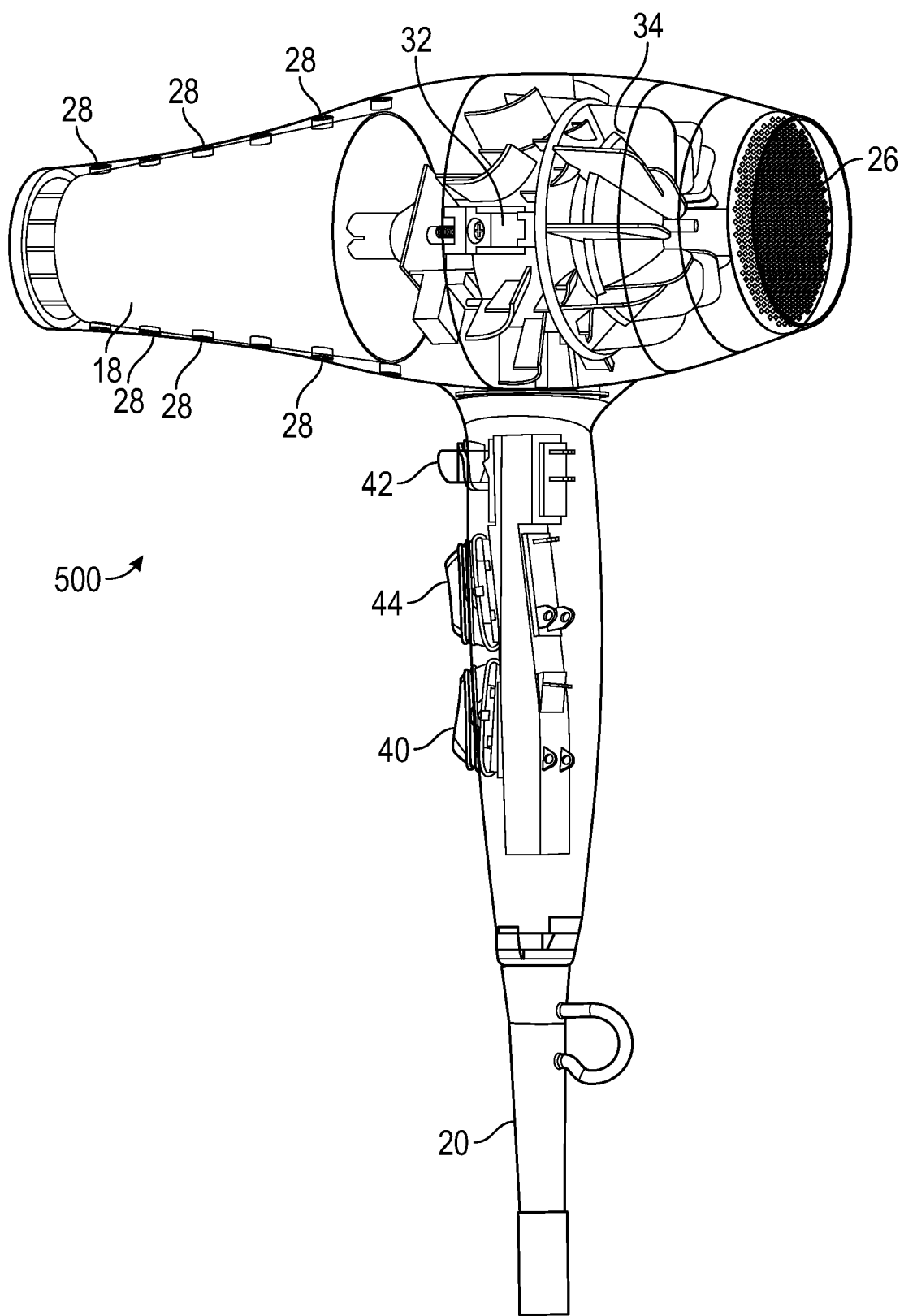
FIG. 23 is a transparent, perspective view of the hair dryer of FIG. 21, illustrating the internal components thereof.

Referring now to FIGS. 18-20, a hair dryer 400 according to another embodiment of the present invention is illustrated. As shown therein, the hair dryer 400 is substantially similar to the hair dryer 10, where like reference numerals designate like parts. Rather than the UV LEDs 28 being arranged in a ring/ annulus and positioned/located rearward of the fan 34 adjacent to the filter of the end cap 26, however, the UV LEDs 28 are arranged in two linear arrays on opposing lateral sides of the housing 16. As best shown in FIG. 20, the UV LEDs 28 may, for example, be mounted to opposed strips 50, 52 that extend horizontally along the housing 16. Similar to the embodiments described above, a transparent cover member 54 (made from the same material as ring 30) encloses the UV LEDs 28 on each side of the housing 16. The cover member 54 is received by, or otherwise forms part of, the housing 16, and allows a user to see that the UV LEDs 28 are illuminated, as discussed above. As best shown in FIG. 20, the rear housing portion 48 includes horizontally-oriented openings 54 or windows that are configured to receive the cover members 54 to enclose the UV LEDs 28 within the housing. In an embodiment, as also disclosed above, the UV LEDs 28 may be mounted to the cover members 54.

Similar to the embodiments described above, the UV LED strips 52, 54 and the UV LEDs 28 retained thereon are oriented and angled in such a manner that a user cannot directly view the emitted light by looking to the inlet 22 or outlet 24. As will be appreciated, operation of the UV LEDs 28 to sanitize the internal components of the hair dryer 400 and the air passing therethrough is also similar to that described above. Importantly, by orienting the UV LEDs in a linear, horizontally-extending array (parallel to the longitudinal axis of the hair dryer 400), the residence time of the air in the UV radiation emitted by the UV LEDs 28 is greater than in the case of the UV LEDs oriented in an annular array. This orientation/arrangement may beneficially increase or optimize the bacteria-killing and/or virus deactivation effectiveness of the hair dryer 400.

Figure 24:
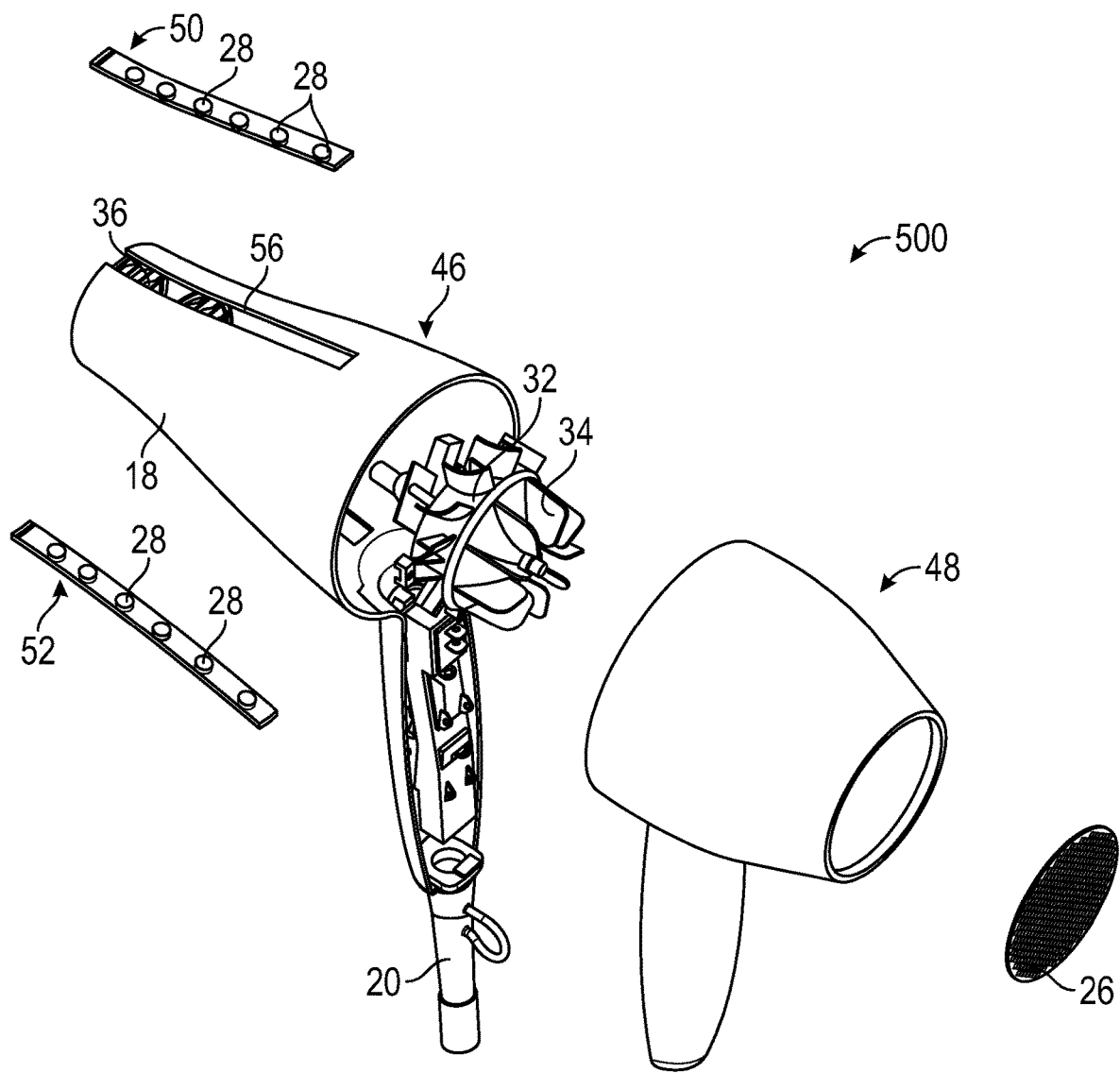
FIG. 24 is an exploded, rear perspective view of the hair dryer of FIG. 21.

FIGS. 21-24 illustrate a similar embodiment of a hair dryer 500, where the UV LEDs 28, the strips 50, 52 and the cover members 54 are located in the top and bottom/underside of the front housing portion 46 (i.e., along the top and bottom of the nozzle 18). In particular, as shown in FIG. 24, the forward end of the nozzle 18 may be formed with recesses or openings 56 in the top and bottom thereof that accommodate the UV LED strips 50, 52 and the transparent cover members 54. Similar to the hair dryer 400, the linear arrangement and positioning of the UV LEDs 28 maximizes the residence time of the airflow in the UV radiation emitting by the UV LEDs, which increases the effectiveness of the irradiation of bacteria, viruses and other contagion or germs.

Figure 25:
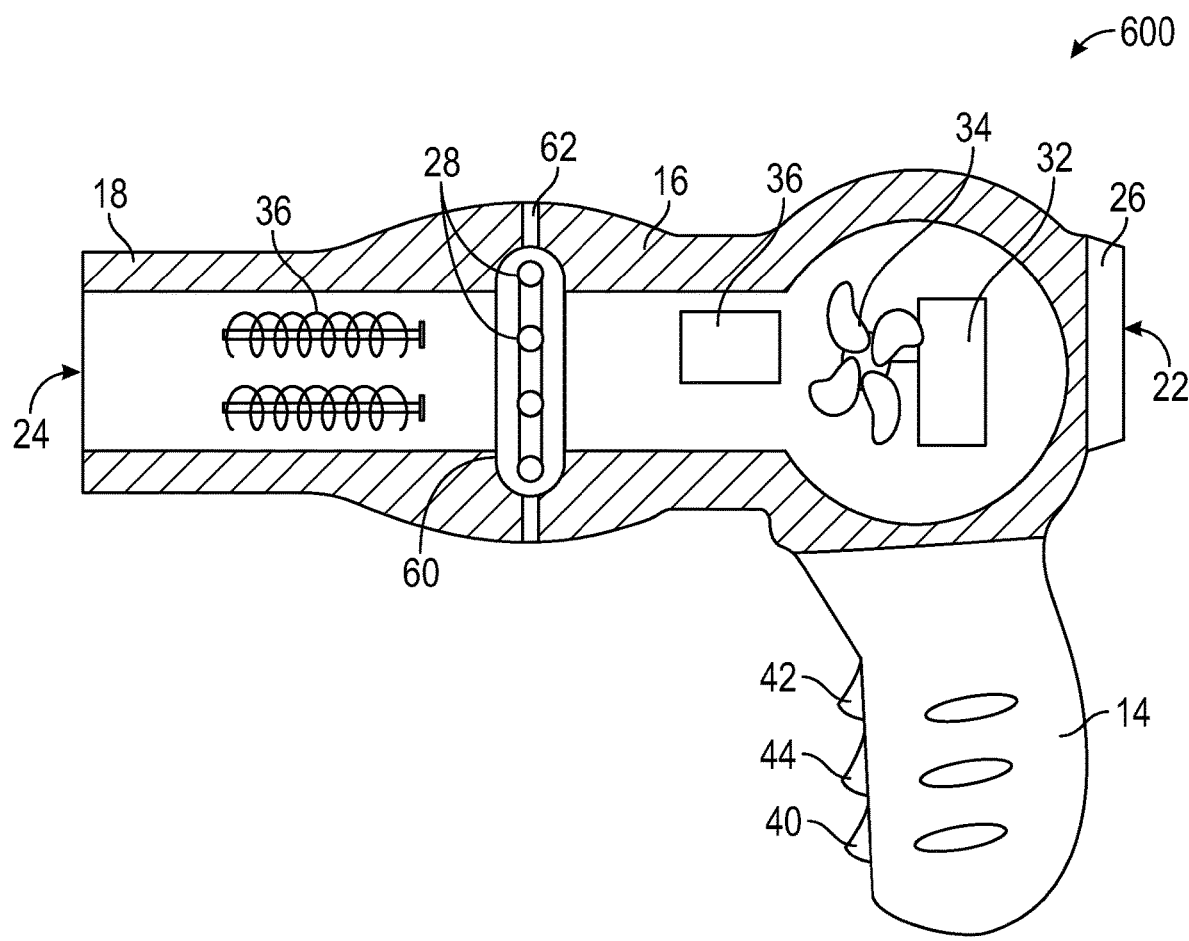
FIG. 25 is side elevational view of a hair dryer according to another embodiment of the present invention.
Figure 26:
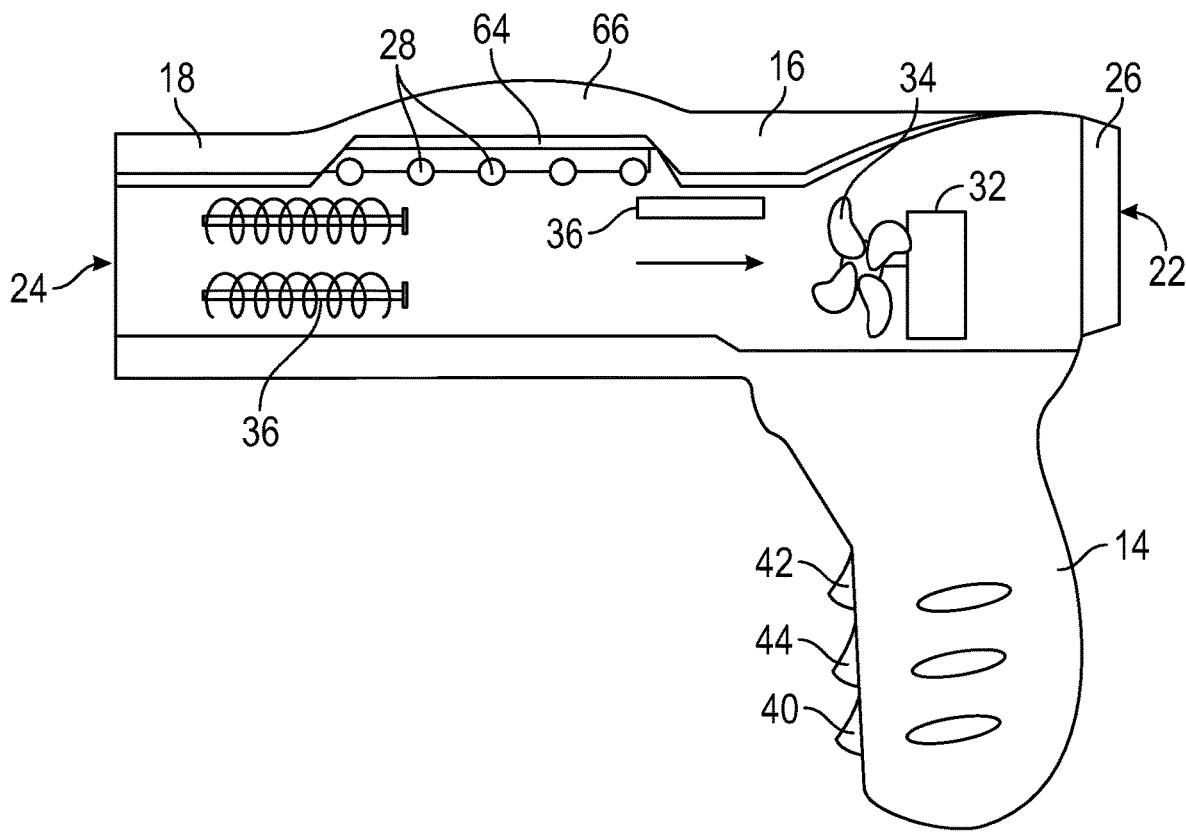
FIG. 26 is a side elevational view of a hair dryer according to another embodiment of the present invention.
Figure 27:
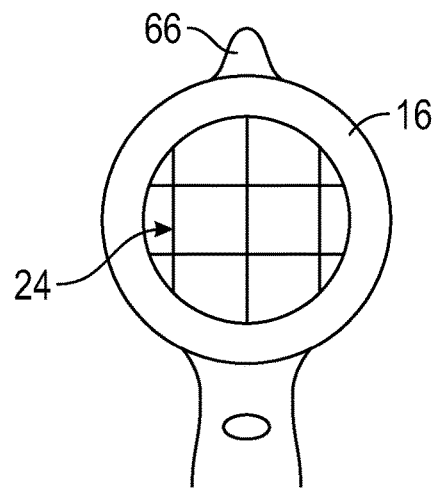
FIG. 27 is a front plan view of the hair dryer of FIG. 26.

Turning finally to FIGS. 25-27, the hair dryers of any of the embodiments disclosed herein may include additional features that inhibits or prevents a user from viewing the UV light emitted by the UV LEDs 28 from the inlet or outlet ends of the hair dryers. For example, FIG. 25 is a simplified, cross-sectional view of a hair dryer 600 that employs an annular array of UV LEDs 28 (similar to that disclosed above in connection with FIGS. 1-17). As shown therein, in an embodiment, the interior passageway of the housing 16 through which air flows has an annular groove or channel 60 within which the annular array of UV LEDs 28 are mounted. This configuration ensures that the UV LEDs 28 are recessed with respect to the interior walls of the housing 16 so that the light emitted by the UV LEDs 28 shines directly across the flow passage, perpendicular to the longitudinal axis of the housing 16. In particular, this configuration ensures that no light from the UV LEDs 28 is directly viewable by looking through the inlet 22 or outlet of the hair dryer 600. Similar to the above, a window, cover or plug 62 may be provided so that UV illumination is visible to a user from outside of the housing. It is contemplated that these features may be incorporated into any of the relevant embodiments disclosed above.

Still further, FIG. 27 is a simplified, cross-sectional view of a hair dryer 700 that employs a linear array of UV LEDs 28 (similar to that disclosed above in connection with FIGS. 18-24). As shown therein, in an embodiment, the interior passageway of the housing 16 through which air flows has a linear groove or channel 64 within which the UV LEDs 28 are mounted. This configuration ensures that the UV LEDs 28 are recessed with respect to the interior walls of the housing 16 so that the light emitted by the UV LEDs 28 shines directly across the flow passage, perpendicular to the longitudinal axis of the housing 16. In particular, this configuration ensures that no light from the UV LEDs 28 is directly viewable by looking through the inlet 22 or outlet of the hair dryer 700. In an embodiment, the outside surface of the hair dryer 700 may have a ridge 66 that accommodates the channel/groove 64. It is contemplated that these features may be incorporated into any of the relevant embodiments disclosed above.

It is contemplated that the hair dryer may have multiple (more than one) annular arrays and/or linear arrays of UV LEDs 28. For example, in an embodiment, a hair dryer may have a plurality of annular arrays of UV LEDs disposed at various longitudinal locations along the housing. In yet other embodiments, a hair dryer may have a combination of both linear and annular arrays of UV LEDs.

In connection with the above, the hair dryers disclosed herein may include a control unit and processor, and associated electrical connections and/or control circuitry necessary to carry out the functions described herein. It is contemplated, however, that more simple electrical and mechanical connections between the switches, buttons and motor, fan, and/or heating elements may be used to carry out the functions described herein.

As described above, the UV LEDs 28 of any of the embodiments described herein sanitize the internal components of the hair dryer and, more importantly, sanitize the air passing through the hair dryer before it exits through the outlet. In particular, intensity/wavelength of the UV LEDs 28 may select to kill bacteria, mold, yeast, fungi, and certain viruses entrained in the airflow passing through the housing and/or on internal components within the housing. The hair dryers of the present invention, therefore, function to disinfect air moving into and out of the hair dryer during use and therefore, to some degree, improves the cleanliness of the air being blown onto a user during use as well as the surrounding air. As will be appreciated therefore, use of the hair dryer 10 of the invention inhibits the spread of bacteria and viruses, such as COVID-19, within hair salons, barber shops and similar settings to a degree heretofore not possible with the use of conventional hair dryers.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A hair dryer, comprising:
    a housing having a handle portion and a nozzle portion;
    a motor within the housing;
    a fan drivingly connected to the motor within the housing;
    a heating element within the housing; and
    at least one ultraviolet light emitting element within the nozzle portion, the at least one ultraviolet light emitting element being configured to irradiate a flow passage of the nozzle portion with ultraviolet light;
    wherein at least a portion of the housing adjacent to the at least one ultraviolet light emitting element is formed from a transparent or translucent material allowing the ultraviolet light to be viewed from exterior to the housing but which prevents a flow of air there through.

2. The hair dryer of claim 1, wherein:
    the nozzle includes an inlet and an outlet; and
    wherein the fan is configured to draw air into the flow passage through the outlet and expel the air from the flow passage through the outlet.

3. The hair dryer of claim 2, wherein:
    the at least one ultraviolet light emitting element is a plurality of ultraviolet light emitting elements.

4. The hair dryer of claim 3, wherein:
    the plurality of ultraviolet light emitting elements are arranged in an annular array.

5. The hair dryer of claim 4, wherein:
    the annular array of ultraviolet light emitting elements is located upstream from the fan.

6. The hair dryer of claim 4, wherein:
    the annular array of ultraviolet light emitting elements is located downstream from the fan.

7. The hair dryer of claim 4, wherein:
    the annular array extends between 180 degrees and 360 degrees.

8. The hair dryer of claim 3, wherein:
the plurality of ultraviolet light emitting elements include a first light emitting element and a second light emitting element positioned on opposing lateral sides of the nozzle portion.

9. The hair dryer of claim 3, wherein:
the plurality of ultraviolet light emitting elements are arranged in a first linear array and a second linear array.

10. The hair dryer of claim 9, wherein:
the first linear array and the second linear array are located on opposing lateral sides of the nozzle portion.

11. The hair dryer of claim 9, wherein:
the first linear array is located on a top of the nozzle portion and the second linear array is located on a bottom of the nozzle portion.

12. The hair dryer of claim 3, wherein:
the light has a wavelength between about 100 nanometers to about 280 nanometers.

13. The hair dryer of claim 1, further comprising:
a switch configured to selectively activate and deactivate the at least one ultraviolet light emitting element.

14. The hair dryer of claim 1, wherein:
each ultraviolet light emitting element is an ultraviolet light emitting diode.

15. The hair dryer of claim 1, wherein:
each ultraviolet light emitting element is recessed within an interior sidewall of the flow passage.

16. A method of sanitizing a flow of air within a hair dryer, the hair dryer having a housing having a handle portion and a nozzle portion, a motor within the housing, a fan drivingly connected to the motor within the housing, and at least one ultraviolet light emitting element within the nozzle portion, the method comprising the steps of:

illuminating a flow passage within the nozzle portion with the at least one ultraviolet light emitting element;
wherein light from the at least one light emitting element is viewable through a portion of the housing formed from a transparent or translucent material; and
wherein the portion of the housing formed from a transparent or translucent material prevents a flow of air therethrough.

17. The method according to claim 16, wherein:
the at least one ultraviolet light emitting element is a plurality of ultraviolet light emitting elements arranged in at least one of an annular array and a linear array.

18. A hair dryer, comprising:
a housing having a handle portion and a nozzle portion;
a motor within the housing;
a fan drivingly connected to the motor within the housing; and
a plurality of light emitting diodes associated with the nozzle portion, the plurality of light emitting diodes each being configured to irradiate a flow passage of the nozzle portion with ultraviolet light;
wherein the plurality of light emitting diodes are arranged in at least one of an annular array and a linear array.

19. The hair dryer of claim 18, wherein:
each of the plurality of light emitting diodes is configured to emit light having wavelength between about 100 nanometers to about 280 nanometers.

20. The hair dryer of claim 1, further comprising:
a window associated with the housing, the window being positioned so as to allow the light emitted by the plurality of light emitting diodes to be viewed through the window.

* * * * *